(12) United States Patent
Kashu et al.

(10) Patent No.: US 10,168,285 B2
(45) Date of Patent: Jan. 1, 2019

(54) PRODUCTION METHOD FOR SEPARATOR SHEET, PRODUCTION METHOD FOR SEPARATOR, SEPARATOR SHEET WOUND BODY, AND SEPARATOR SHEET PRODUCTION DEVICE

(71) Applicant: Sumitomo Chemical Company, Limited, Tokyo (JP)

(72) Inventors: Koji Kashu, Niihama (JP); Yusuke Kon, Daegu (KR); Tatsuya Sakamoto, Niihama (JP); Jian Wang, Daegu (KR)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/517,199

(22) PCT Filed: Sep. 18, 2015

(86) PCT No.: PCT/JP2015/076650
§ 371 (c)(1),
(2) Date: Apr. 6, 2017

(87) PCT Pub. No.: WO2016/056378
PCT Pub. Date: Apr. 14, 2016

(65) Prior Publication Data
US 2017/0307543 A1 Oct. 26, 2017

(30) Foreign Application Priority Data
Oct. 10, 2014 (JP) .................................. 2014-209414
Jan. 30, 2015 (WO) .................. PCT/JP2015/052749

(51) Int. Cl.
*H01M 2/14* (2006.01)
*G01N 21/894* (2006.01)
*H01M 10/0525* (2010.01)

(52) U.S. Cl.
CPC .......... *G01N 21/894* (2013.01); *H01M 2/145* (2013.01); *H01M 10/0525* (2013.01)

(58) Field of Classification Search
CPC ........................................................ H01M 2/14
See application file for complete search history.

(56) References Cited

U.S. PATENT DOCUMENTS 3,806,015 A    4/1974    Kachioff et al.
5,523,848 A    6/1996    Musso et al.
(Continued)

FOREIGN PATENT DOCUMENTS

CN    1804601 A    7/2006
CN    1873398 A    12/2006
(Continued)

OTHER PUBLICATIONS

Office Action dated Sep. 25, 2017 in CN Application No. 201580054773.
(Continued)

*Primary Examiner* — Jacob B Marks
(74) *Attorney, Agent, or Firm* — Panitch Schwarze Belisario & Nadel LLP

(57) ABSTRACT

A separator producing method includes the steps of: winding up, around a core (81, 53), a separator (12a, 12b) having a defect (D) detected; and providing a defect code (DC2) including information on a position of the defect (D) in the longitudinal direction of the separator (12a, 12b) on (i) the outermost portion (86, 86b) of the separator (12a, 12b), wound around the core (81, 53), or (ii) the core (81, 53), around which the separator (12a, 12b) is wound.

9 Claims, 16 Drawing Sheets

(56) References Cited

U.S. PATENT DOCUMENTS

| | | | |
|---|---|---|---|
| 6,219,930 | B1 | 4/2001 | Reid |
| 2004/0251176 | A1 | 12/2004 | Alonso et al. |
| 2006/0164647 | A1 | 7/2006 | Shibata |
| 2008/0087149 | A1 | 4/2008 | Ohashi |
| 2010/0294418 | A1 | 11/2010 | Yura et al. |
| 2011/0085125 | A1 | 4/2011 | Kimura et al. |
| 2012/0002153 | A1 | 1/2012 | Kimura et al. |
| 2012/0002154 | A1 | 1/2012 | Kimura et al. |
| 2012/0028067 | A1 | 2/2012 | Izaki et al. |
| 2012/0055607 | A1 | 3/2012 | Kitagawa et al. |
| 2012/0055608 | A1 | 3/2012 | Kitagawa et al. |
| 2012/0055621 | A1 | 3/2012 | Goto et al. |
| 2012/0055622 | A1 | 3/2012 | Kitagawa et al. |
| 2012/0055623 | A1 | 3/2012 | Kitagawa et al. |
| 2012/0056211 | A1 | 3/2012 | Kitagawa et al. |
| 2012/0056340 | A1 | 3/2012 | Kitagawa et al. |
| 2012/0057104 | A1 | 3/2012 | Kitagawa et al. |
| 2012/0057107 | A1 | 3/2012 | Kitagawa et al. |
| 2012/0057231 | A1 | 3/2012 | Goto et al. |
| 2012/0057232 | A1 | 3/2012 | Goto et al. |
| 2012/0058291 | A1 | 3/2012 | Kitagawa et al. |
| 2012/0058321 | A1 | 3/2012 | Goto et al. |
| 2013/0100529 | A1 | 4/2013 | Kitagawa et al. |
| 2013/0114139 | A1 | 5/2013 | Kitagawa et al. |
| 2013/0169956 | A1 | 7/2013 | Cano Cediel et al. |
| 2014/0014762 | A1 | 1/2014 | Ichinomiya et al. |
| 2014/0186568 | A1 | 7/2014 | Kitagawa et al. |
| 2014/0248525 | A1* | 9/2014 | Iwai ............... H01M 2/1686 429/144 |
| 2014/0287255 | A1 | 9/2014 | Izaki et al. |
| 2015/0183199 | A1 | 7/2015 | Kitagawa et al. |
| 2016/0054494 | A1 | 2/2016 | Kitagawa et al. |
| 2016/0103258 | A1 | 4/2016 | Kitagawa et al. |
| 2016/0377416 | A1 | 12/2016 | Reid et al. |
| 2017/0317327 | A1 | 11/2017 | Kashu et al. |

FOREIGN PATENT DOCUMENTS

| | | | |
|---|---|---|---|
| CN | 101468543 | A | 7/2009 |
| CN | 101925944 | A | 12/2010 |
| CN | 101980797 | A | 2/2011 |
| CN | 101981438 | A | 2/2011 |
| CN | 102043280 | A | 5/2011 |
| CN | 102341733 | A | 2/2012 |
| CN | 102385086 | A | 3/2012 |
| CN | 102385087 | A | 3/2012 |
| CN | 102866168 | A | 1/2013 |
| JP | H8101130 | A | 4/1996 |
| JP | 2002228429 | A | 8/2002 |
| JP | 2004338406 | A | 12/2004 |
| JP | 2004338409 | A | 12/2004 |
| JP | 2006194721 | A | 7/2006 |
| JP | 2006220527 | A | 8/2006 |
| JP | 200882910 | A | 4/2008 |
| JP | 2008116437 | A | 5/2008 |
| JP | 2009133741 | A | 6/2009 |
| JP | 2009244063 | A | 10/2009 |
| JP | 201032346 | A | 2/2010 |
| JP | 2011220967 | A | 11/2011 |
| JP | 201333033 | A | 2/2013 |

OTHER PUBLICATIONS

Office Action dated Oct. 10, 2017 in CN Application No. 201580054771.1.

Int'l Search Report dated Dec. 8, 2015 in Int'l Application No. PCT/JP2015/076652.

Int'l Search Report dated Dec. 8, 2015 in Int'l Application No. PCT/JP2015/076651.

Int'l Search Report dated Dec. 8, 2015 in Int'l Application No. PCT/JP2015/076650.

Int'l Search Report dated Apr. 14, 2015 in Int'l Application No. PCT/JP2015/052749.

Office Action dated Jun. 14, 2016 in JP Application No. 2016-520128.

Decision to Grant dated Sep. 6, 2016 in JP Application No. 2016-520128.

Office Action dated Jun. 14, 2016 in JP Application No. 2016-520129.

Decision to Grant dated Sep. 6, 2016 in JP Application No. 2016-520129.

Office Action dated Jun. 14, 2016 in JP Application No. 2016-520115.

Decision to Grant dated Sep. 6, 2016 in JP Application No. 2016-520115.

Int'l Preliminary Report on Patentability dated Apr. 20, 2017 in Int'l Application No. PCT/JP2015/076652.

Int'l Preliminary Report on Patentability dated Apr. 20, 2017 in Int'l Application No. PCT/JP2015/076651.

Int'l Preliminary Report on Patentability dated Apr. 20, 2017 in Int'l Application No. PCT/JP2015/076650.

Int'l Preliminary Report on Patentability dated Apr. 20, 2017 in Int'l Application No. PCT/JP2015/052749.

Office Action dated Apr. 7, 2015 in JP Application No. 2015-506030 (Partial Translation).

Office Action dated Jan. 8, 2018 in U.S. Appl. No. 15/517,818, by Kashu.

Office Action dated Feb. 11, 2018 in CN Application No. 201580054773.0.

Office Action dated Nov. 28, 2017 in CN Application No. 201580056172.3.

Office Action dated Sep. 19, 2018 in U.S. Appl. No. 15/517,249 by Watanabe.

* cited by examiner

PRODUCTION METHOD FOR SEPARATOR SHEET, PRODUCTION METHOD FOR SEPARATOR, SEPARATOR SHEET WOUND BODY, AND SEPARATOR SHEET PRODUCTION DEVICE

CROSS-REFERENCE TO RELATED APPLICATION

This application is a Section 371 of International Application No. PCT/JP2015/076650, filed Sep. 18, 2015, which was published in the Japanese language on Apr. 14, 2016 under International Publication No. WO 2016/056378 A1, and the disclosure of which is incorporated herein by reference.

TECHNICAL FIELD

The present invention relates to (i) a method for producing a separator original sheet for use in a lithium-ion secondary battery, (ii) a method for producing a separator, (iii) a separator roll, (iv) a separator original sheet roll, and (v) an apparatus for producing a separator original sheet.

BACKGROUND ART

There has been known a deficiency inspecting device for a sheet-shaped product including an optical film (Patent Literature 1). The deficiency inspecting device receives information on a deficiency from a protective film inspecting section, and forms a data code (for example, a two-dimensional code or a QR Code [registered trademark]) having a fixed pitch and indicative of the deficiency. The deficiency inspecting device forms such a data code on a surface at an end of a PVA film original sheet together with information on the position and production identification.

CITATION LIST

Patent Literature

[Patent Literature 1] Japanese Patent Application Publication, Tokukai, No. 2008-116437 (Publication Date: May 22, 2008)

SUMMARY OF INVENTION

Technical Problem

Production of a separator for use in a lithium-ion secondary battery, however, suffers from a defect in a separator original sheet. Enormous efforts are expended to specify the position of such a defect in a separator original sheet.

The code data described in Patent Literature 1, which is recorded on a surface at an end, may be inside a roll including a core and a separator wound around the core. In such a case, the code data cannot be read, making it difficult to specify the position of a defect in a separator wound around a core.

It is an object of the present invention to provide a method for producing a separator original sheet, a method for producing a separator, a separator roll, a separator original sheet roll, and a separator original sheet producing apparatus each of which allows the position of a defect in a separator wound around a core to be easily specified.

Solution to Problem

In order to attain the above object, a separator producing method in accordance with the present invention includes the steps of: winding up, around a core, a separator having a defect detected; and providing a first defect code, including information on a first position of the defect which first position is a position in a longitudinal direction of the separator, on (i) the core, (ii) a side surface of the separator wound around the core, (iii) an outer layer of the separator wound around the core, or (iv) a package of a roll including the core and the separator wound around the core.

The above feature involves providing a first defect code, including information on a first position of a defect which first position is a position in the longitudinal direction of a separator, on (i) the core, (ii) a side surface of the separator wound around the core, (iii) an outer layer of the separator wound around the core, or (iv) a package of a roll including the core and the separator wound around the core. With the above feature, reading a first defect code, which can be exposed to the outside of a roll, makes it possible to easily specify the position of a defect in a separator wound around a core.

In order to attain the above object, a separator original sheet producing method in accordance with the present invention includes the steps of: winding up, around a core, a separator original sheet having a defect detected; and providing a first defect code, including information on a first position of the defect which first position is a position in a longitudinal direction of the separator original sheet, on (i) the core, (ii) a side surface of the separator original sheet wound around the core, (iii) an outer layer of the separator original sheet wound around the core, or (iv) a package of a roll including the core and the separator original sheet wound around the core.

The above feature involves providing a first defect code, including information on a first position of a defect which first position is a position in the longitudinal direction of a separator original sheet, on (i) the core, (ii) a side surface of the separator original sheet wound around the core, (iii) an outer layer of the separator original sheet wound around the core, or (iv) a package of a roll including the core and the separator original sheet wound around the core. With the above feature, reading a first defect code, which can be exposed to the outside of a roll, makes it possible to easily specify the position of a defect in a separator original sheet wound around a core.

The separator original sheet producing method in accordance with the present invention may preferably further include the step of providing a second defect code, including information on a second position of the defect which second position is a position in a width direction of the separator original sheet, at each of opposite widthwise ends of the separator original sheet.

With the above arrangement, it is only necessary to normally read at least one of the second defect codes at the opposite ends. This makes it possible to read a second defect code more reliably. In a case where, for example, one of the widthwise ends of a separator original sheet has been wrinkled or one of the second defect codes has disappeared, it is possible to read the other second defect code.

The separator original sheet producing method in accordance with the present invention may preferably be arranged such that the second defect code is provided at a position indicative of the first position.

The above arrangement makes it possible to (i), with reference to a first defect code, roughly locate the position of a defect in the longitudinal direction of a separator original sheet, which is porous and tends to be stretched in the longitudinal direction, and (ii) accurately specify the position of the defect with reference to the position at which a second defect code is provided.

In order to attain the above object, a separator producing method in accordance with the present invention includes the steps of: (a) cutting a separator original sheet, having a defect detected, in a longitudinal direction of the separator original sheet into a plurality of separators; (b) winding up, around a core, a separator among the plurality of separators which separator has the defect; and (c) providing a first defect code, including information on a first position of the defect which first position is a position in a longitudinal direction of the separator, on (i) the core, (ii) a side surface of the separator wound around the core, (iii) an outer layer of the separator wound around the core, or (iv) a package of a roll including the core and the separator wound around the core.

The above feature involves providing a first defect code, including information on a first position of a defect which first position is a position in the longitudinal direction of a separator, on (i) the core, (ii) a side surface of the separator wound around the core, (iii) an outer layer of the separator wound around the core, or (iv) a package of a roll including the core and the separator wound around the core. With the above feature, reading a first defect code, which can be exposed to the outside of a roll, makes it possible to easily specify the position of a defect in a separator wound around a core.

The separator producing method in accordance with the present invention may preferably further include the step of (d) providing a second defect code, including information on a second position of the defect which second position is a position in a width direction of the separator, at each of opposite widthwise ends of the separator.

With the above arrangement, it is only necessary to normally read at least one of the second defect codes at the opposite ends. This makes it possible to read a second defect code more reliably. In a case where, for example, one of the widthwise ends of a separator original sheet has been wrinkled or one of the second defect codes has disappeared, it is possible to read the other second defect code.

The separator producing method in accordance with the present invention may preferably be arranged such that the second defect code is provided at a position indicative of a position of the defect which position is a position in the longitudinal direction of the separator original sheet.

The above arrangement makes it possible to (i), with reference to a first defect code, roughly locate the position of a defect in the longitudinal direction of a separator, which is porous and tends to be stretched in the longitudinal direction, and (ii) on the basis of the respective positions of second defect codes at the opposite widthwise ends of the separator original sheet, easily provide a mark for accurately specifying the position of the defect in the longitudinal direction of the separator at a portion corresponding to the defect in the separator (which is among the plurality of separators and which has the defect).

The separator producing method in accordance with the present invention may preferably further include the steps of: (e) providing the separator with a mark for specifying a position of the defect; (f) sensing the mark while carrying out an operation of winding off the separator, which is present after the step (c), and winding up the separator again; and (g) in accordance with the sensing of the mark, stopping the operation and removing the defect.

The above arrangement makes it possible to (i), with reference to a first defect code, roughly locate the position of a defect in the longitudinal direction of a separator, which is porous and tends to be stretched in the longitudinal direction, and (ii) accurately specify the position of the defect with reference to the position at which a mark is provided.

The separator producing method in accordance with the present invention may preferably be arranged such that in the step (f), the first defect code is read, and when the defect has become close to the outer layer, the operation is slowed in correspondence with the first position.

The above arrangement makes it possible to easily specify the first position when the separator is wound off and wound up again.

The separator producing method in accordance with the present invention may preferably be arranged such that the step (e) is carried out by attaching a label.

The above arrangement makes it possible to easily specify the position of a defect in a separator with use of an attached label.

In order to attain the above object, a separator roll in accordance with the present invention includes: a core; a separator having a defect and wound around the core; and a first defect code that is provided on (i) the core, (ii) a side surface of the separator wound around the core, (iii) an outer layer of the separator wound around the core, or (iv) a package of a roll including the core and the separator wound around the core and that includes information on a first position of the defect which first position is a position in a longitudinal direction of the separator.

The above feature involves providing a first defect code, including information on a first position of a defect which first position is a position in the longitudinal direction of a separator, on (i) the core, (ii) a side surface of the separator wound around the core, (iii) an outer layer of the separator wound around the core, or (iv) a package of a roll including the core and the separator wound around the core. With the above feature, reading a first defect code, which can be exposed to the outside of a roll, makes it possible to easily specify the position of a defect in a separator wound around a core.

In order to attain the above object, a separator original sheet roll in accordance with the present invention includes: a core; a separator original sheet having a defect and wound around the core; and a first defect code that is provided on (i) the core, (ii) a side surface of the separator original sheet wound around the core, (iii) an outer layer of the separator original sheet wound around the core, or (iv) a package of a roll including the core and the separator original sheet wound around the core and that includes information on a first position of the defect which first position is a position in a longitudinal direction of the separator original sheet.

The above feature involves providing a first defect code, including information on a first position of a defect which first position is a position in the longitudinal direction of a separator original sheet, on (i) the core, (ii) a side surface of the separator original sheet wound around the core, (iii) an outer layer of the separator original sheet wound around the core, or (iv) a package of a roll including the core and the separator original sheet wound around the core. With the above feature, reading a first defect code, which can be exposed to the outside of a roll, makes it possible to easily specify the position of a defect in a separator original sheet wound around a core.

The separator original sheet roll in accordance with the present invention may preferably further include: a second defect code that is provided at each of opposite widthwise ends of the separator original sheet and that includes information on a second position of the defect which second position is a position in a width direction of the separator original sheet.

With the above arrangement, it is only necessary to normally read at least one of the second defect codes at the opposite ends. This makes it possible to read a second defect code more reliably. In a case where, for example, one of the widthwise ends of a separator original sheet has been wrinkled or one of the second defect codes has disappeared, it is possible to read the other second defect code.

In order to attain the above object, a separator original sheet producing apparatus in accordance with the present invention includes: a wind-up section configured to wind up, around a core, a separator original sheet having a defect detected; and a first defect code providing section configured to provide a first defect code, including information on a first position of the defect which first position is a position in a longitudinal direction of the separator original sheet, on (i) the core, (ii) a side surface of the separator original sheet wound around the core, (iii) an outer layer of the separator original sheet wound around the core, or (iv) a package of a roll including the core and the separator original sheet.

The above feature involves providing a first defect code, including information on a first position of a defect which first position is a position in the longitudinal direction of a separator original sheet, on (i) the core, (ii) a side surface of the separator wound around the core, (iii) an outer layer of the separator wound around the core, or (iv) a package of a roll including the core and the separator wound around the core. With the above feature, reading a first defect code, which can be exposed to the outside of a roll, makes it possible to easily specify the position of a defect in a separator original sheet wound around a core.

In order to attain the above object, a separator producing method in accordance with the present invention includes the steps of: cutting a separator original sheet, having a defect detected, in a longitudinal direction of the separator original sheet into a plurality of separators; providing a separator among the plurality of separators, which separator has the defect, with a mark for specifying a position of the defect; and winding up, around a core, the separator, which is provided with the mark.

The above feature involves winding up, around a core, a separator having a mark provided so as to specify the position of a defect. The mark thus appears when the separator is would off to a defective portion. This makes it possible to easily specify the position of a defect in a separator wound off the core.

In order to attain the above object, a separator roll in accordance with the present invention includes: a core; a separator having a defect and wound around the core; and a mark provided on the separator so as to specify a position of the defect.

The above feature involves providing a mark for specifying the position of a defect to a separator wound around a core. The mark thus appears when the separator is would off to a defective portion. This makes it possible to easily specify the position of a defect in a separator wound off the core.

Advantageous Effects of Invention

The present invention produces the effect of easily specifying the position of a defect in a separator wound around a core.

DESCRIPTION OF EMBODIMENTS

The following description will discuss embodiments of the present invention in detail.

Embodiment 1

The following description will discuss, in order, a lithium-ion secondary battery, a separator, a heat-resistant separator, a heat-resistant separator producing method, a slitting apparatus, and a cutting device each in accordance with Embodiment 1.

(Lithium-Ion Secondary Battery)

A nonaqueous electrolyte secondary battery, typically a lithium-ion secondary battery, has a high energy density, and is therefore currently widely used not only as batteries for use in devices such as personal computers, mobile phones, and mobile information terminals, and for use in moving bodies such as automobiles and airplanes, but also as stationary batteries contributing to stable power supply.

Figure 1:
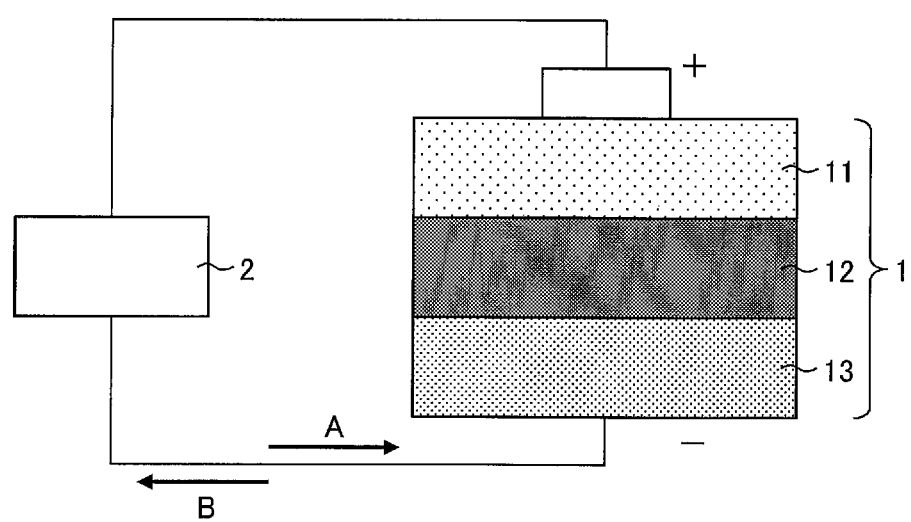
FIG. 1 is a diagram schematically illustrating a cross-sectional configuration of a lithium-ion secondary battery in accordance with Embodiment 1.

FIG. 1 is a diagram schematically illustrating a cross-sectional configuration of a lithium-ion secondary battery 1. As illustrated in FIG. 1, the lithium-ion secondary battery 1 includes a cathode 11, a separator 12, and an anode 13. Between the cathode 11 and the anode 13, an external device 2 is connected outside the lithium-ion secondary battery 1. While the lithium-ion secondary battery 1 is being charged, electrons move in a direction A. Meanwhile, while the lithium-ion secondary battery 1 is being discharged, electrons move in a direction B.

(Separator)

The separator 12 is provided so as to be sandwiched between the cathode 11 (as a positive electrode) and the anode 13 (as a negative electrode) of the lithium-ion secondary battery 1. While separating the cathode 11 and the anode 13, the separator 12 allows lithium ions to move between the cathode 11 and the anode 13. The separator 12 contains, for example, a polyolefin (for example, polyethylene or polypropylene) as a material thereof.

Figure 2:
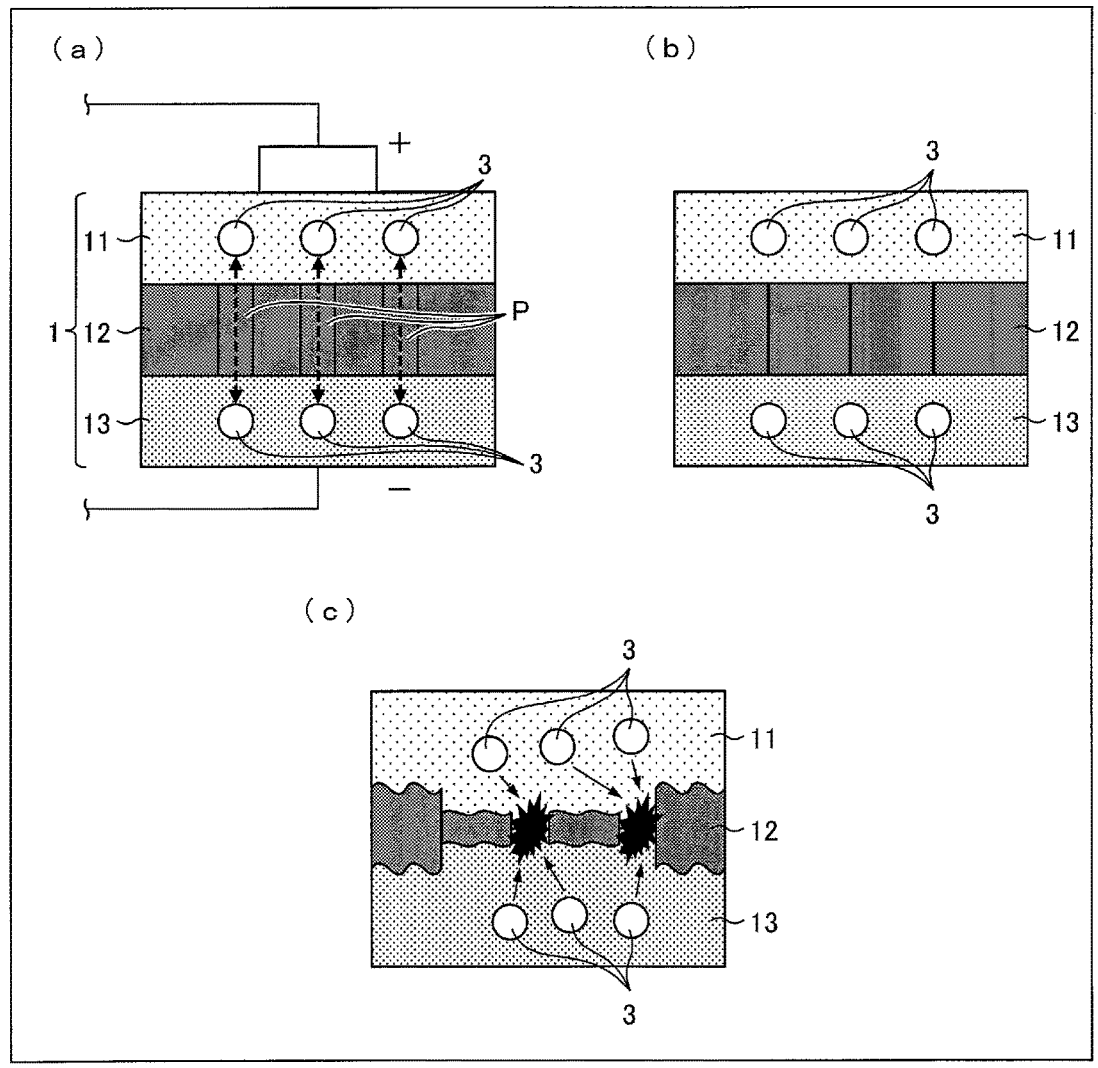
FIG. 2 provides diagrams schematically illustrating details of the configuration of the lithium-ion secondary battery illustrated in FIG. 1.

FIG. 2 provides diagrams schematically illustrating details of the configuration of the lithium-ion secondary battery 1 illustrated in FIG. 1. (a) of FIG. 2 illustrates a normal configuration. (b) of FIG. 2 illustrates a state in which the temperature of the lithium-ion secondary battery 1 has risen. (c) of FIG. 2 illustrates a state in which the temperature of the lithium-ion secondary battery 1 has sharply risen.

As illustrated in (a) of FIG. 2, the separator 12 is provided with many pores P. Normally, lithium ions 3 in the lithium-ion secondary battery 1 can move back and forth through the pores P.

Note here that there may be, for example, a case where the lithium-ion secondary battery 1 increases in temperature due to, for example, (i) overcharge of the lithium-ion secondary battery 1 or (ii) a large current caused by a short circuit having occurred in an external device. In such cases, the separator 12 melts or softens, and the pores P are blocked as illustrated in (b) of FIG. 2. As a result, the separator 12 shrinks. This stops the movement of the lithium ions 3, and consequently stops the increase in temperature (described earlier).

Note, however, that the separator 12 suddenly shrinks in a case where the lithium-ion secondary battery 1 sharply increases in temperature. In this case, as illustrated in (c) of FIG. 2, the separator 12 may be broken. Then, the lithium ions 3 leak out from the separator 12 which has been broken, so that the lithium ions 3 do not stop moving back and forth. Thus, the increase in temperature continues.

(Heat-Resistant Separator)

Figure 3:
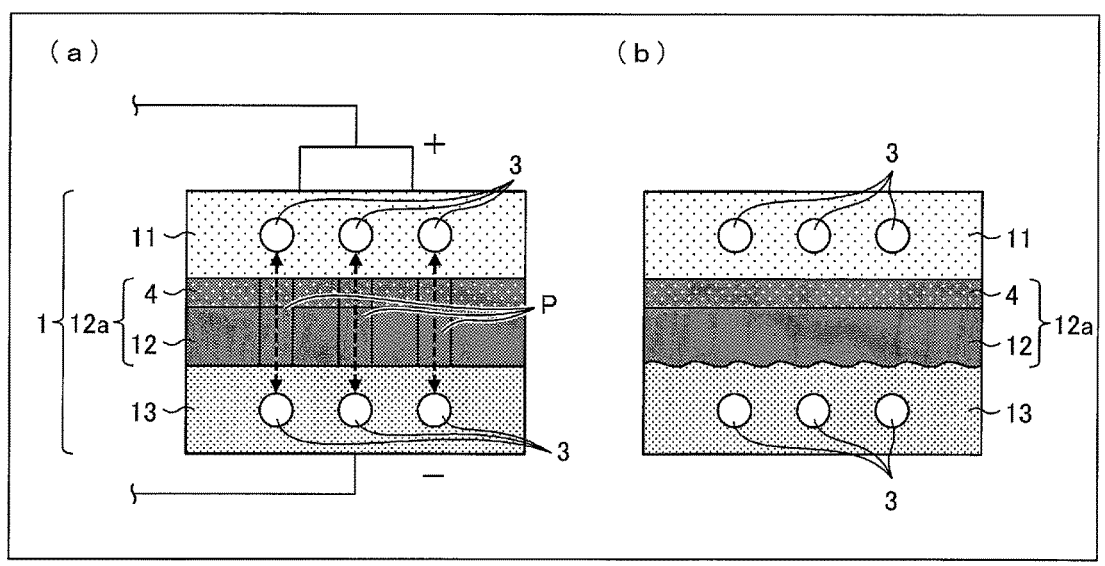
FIG. 3 provides diagrams schematically illustrating another configuration of the lithium-ion secondary battery illustrated in FIG. 1.

FIG. 3 provides diagrams schematically illustrating another configuration of the lithium-ion secondary battery 1 illustrated in FIG. 1. (a) of FIG. 3 illustrates a normal configuration, and (b) of FIG. 3 illustrates a state in which the temperature of the lithium-ion secondary battery 1 has sharply risen.

As illustrated in (a) of FIG. 3, the lithium-ion secondary battery 1 can further include a heat-resistant layer 4. The heat-resistant layer 4 and the separator 12 form a heat-resistant separator 12a (separator). The heat-resistant layer 4 is laminated on one surface of the separator 12 which surface is on the cathode 11 side. The heat-resistant layer 4 may alternatively be laminated on (i) a surface of the separator 12 which surface is on the anode 13 side or on (ii) both surfaces of the separator 12. Further, the heat-resistant layer 4 is provided with pores that are similar to the pores P. Normally, lithium ions 3 move back and forth through the pores P and the pores of the heat-resistant layer 4. The heat-resistant layer 4 contains, for example, wholly aromatic polyamide (aramid resin) as a material thereof.

As illustrated in (b) of FIG. 3, even in a case where the temperature of the lithium-ion secondary battery 1 has sharply risen and accordingly the separator 12 has melted or softened, the shape of the separator 12 is maintained because the heat-resistant layer 4 supports the separator 12. Thus, such a sharp increase in temperature merely results in melting or softening of the separator 12 and consequent blocking of the pores P. This stops the movement of the lithium ions 3, and consequently stops overdischarge and overcharge (described earlier). The separator 12 is thus prevented from being broken.

(Steps of Producing Heat-Resistant Separator Original Sheet (Separator Original Sheet))

How to produce the heat-resistant separator 12a of the lithium-ion secondary battery 1 is not particularly limited. The heat-resistant separator 12a can be produced by a publicly known method. The following discussion assumes a case where the separator 12 contains polyethylene as a main material. However, even in a case where the separator 12 contains another material, the similar steps can still be applied to production of the separator 12.

For example, it is possible to employ a method including the steps of first forming a film by adding a plasticizer to a thermoplastic resin, and then removing the plasticizer with use of an appropriate solvent. For example, in a case where the separator 12 is made of a polyethylene resin containing an ultrahigh molecular weight polyethylene, it is possible to produce a separator 12 by the following method.

This method includes (1) a kneading step of obtaining a polyethylene resin composition by kneading an ultrahigh molecular weight polyethylene and an inorganic filler such as calcium carbonate, (2) a rolling step of forming a film from the polyethylene resin composition, (3) a removal step of removing the inorganic filler from the film obtained in the step (2), and (4) a stretching step of obtaining a separator 12 by stretching the film obtained in the step (3).

In the removal step, many fine pores are provided in the film. The fine pores of the film stretched in the stretching step become the above-described pores P. The separator 12 formed as a result is a polyethylene microporous film having a prescribed thickness and a prescribed air permeability.

Note that the kneading step may involve kneading (i) 100 parts by weight of the ultrahigh molecular weight polyethylene, (ii) 5 parts by weight to 200 parts by weight of a low-molecular weight polyolefin having a weight-average molecular weight of 10000 or less, and (iii) 100 parts by weight to 400 parts by weight of the inorganic filler.

Thereafter, in a coating step, the heat-resistant layer 4 is formed on a surface of the separator 12. For example, on the separator 12, an aramid/NMP (N-methylpyrrolidone) solution (coating solution) is applied, and thereby, the heat-resistant layer 4 that is an aramid heat-resistant layer is formed. The heat-resistant layer 4 can be provided on only one surface or both surfaces of the separator 12. Alternatively, the heat-resistant layer 4 can be formed by using alumina/carboxymethyl cellulose for coating.

The method for coating the separator 12 with a coating solution is not particularly limited as long as uniform wet coating can be performed by the method. The method can be a conventionally publicly known method such as a capillary coating method, a spin coating method, a slit die coating method, a spray coating method, a dip coating method, a roll coating method, a screen printing method, a flexo printing method, a bar coater method, a gravure coater method, or a die coater method. The heat-resistant layer 4 has a thickness which can be controlled by adjusting (i) the thickness of a coating wet film, (ii) the solid-content concentration (which is the sum of concentrations of a binder and a filler in the coating solution), and/or (iii) the ratio of the filler to the binder.

It is possible to use a resin film, a metal belt, a drum or the like as a support with which the separator 12 is fixed or transferred in coating.

Figure 4:
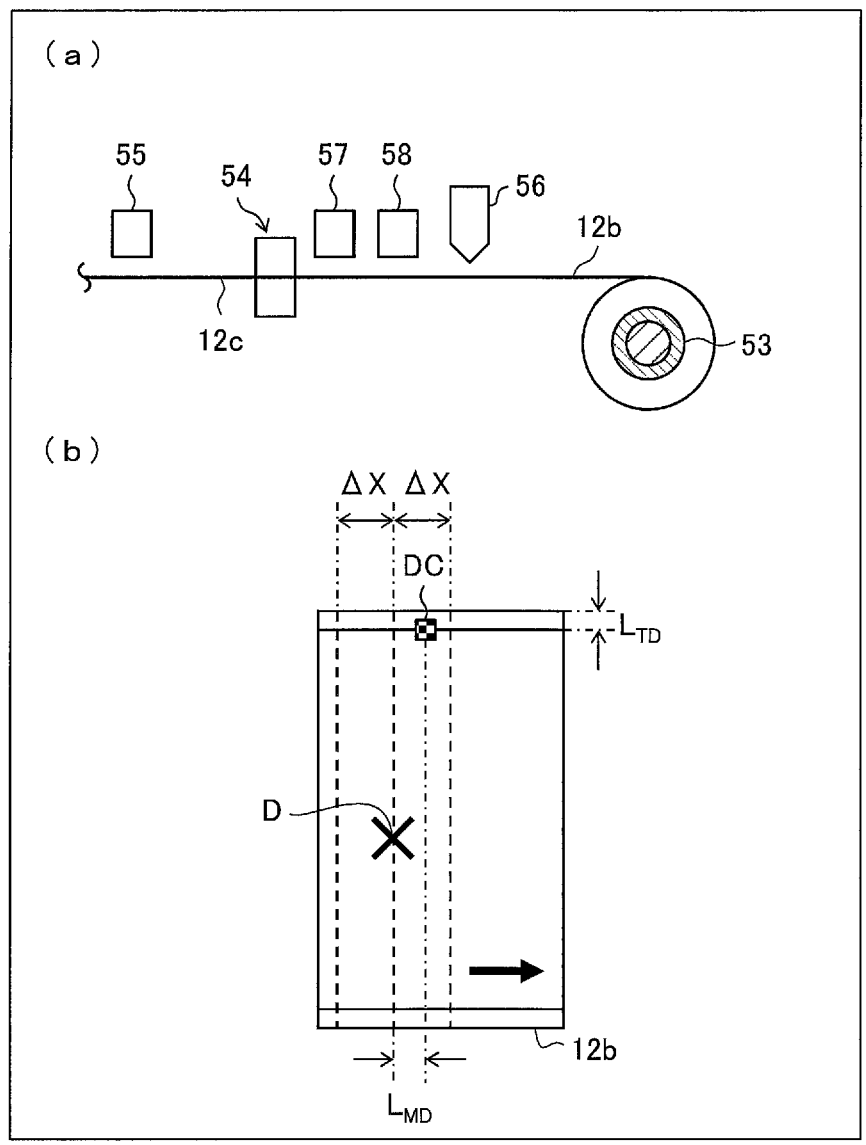
FIG. 4 provides diagrams schematically illustrating a defect detecting step and a defect information recording step both included in a method for marking a defect in a separator original sheet.

This operation allows for production of a heat-resistant separator original sheet 12b (separator original sheet, separator) which is a separator original sheet 12c on which the heat-resistant layer 4 is laminated (forming step) (see FIG. 4). The heat-resistant separator original sheet 12b thus produced is wound around a core 53 having a cylindrical shape (see FIG. 4). Note that the subject to be produced by the above production method is not limited to the heat-resistant separator original sheet 12b. The above production method does not necessarily include the coating step. In this case, the subject to be produced is a separator original sheet 12c.

In a case where during production of a heat-resistant separator for use in a lithium-ion secondary battery, an inspecting device has detected a defect in a coating step of preparing a heat-resistant separator original sheet including a separator original sheet coated with a heat-resistant layer, the original sheet having the defect is provided with a line drawn with a marker before the heat-resistant separator original sheet is wound up. In the subsequent slitting step, the heat-resistant separator original sheet is wound off. Then, when an operator sees the line drawn with the marker on the heat-resistant separator original sheet wound off, the operator stops the operation of winding off the heat-resistant separator original sheet. Next, the operator visually checks the position, along the width of the heat-resistant separator original sheet, of the defect indicated by the line drawn with the marker. Next, that portion of the heat-resistant separator original sheet on which the line is drawn with the marker is cut by a cutting device lengthwise to form a plurality of heat-resistant separators. Then, the operator attaches, to one of the heat-resistant separators, a piece of tape in such a manner that (i) the tape coincides with the lengthwise position on the heat-resistant separator at which position the defect indicated by the line drawn with the marker is present and that (ii) the tape extends beyond a side of the heat-resistant separator. The heat-resistant separator, to which the tape is attached in such a manner that the tape extends beyond a side of the heat-resistant separator, is wound up around a wind-up roller.

Next, the heat-resistant separator wound up around the wind-up roller is wound off from the wind-up roller and then wound up around an additional wind-up roller in an additional wind-up step. When an operator sees the tape in the additional wind-up step, the operator stops the operation of the additional wind-up step. The operator then cuts off, in the width direction, that portion of the heat-resistant separator at which the defect indicated by the tape is present, and removes that portion from the rest. Next, the heat-resistant separator on the side of the wind-up roller is connected with the heat-resistant separator on the side of the additional wind-up roller. Then, the operation of the additional wind-up step is resumed, so that the heat-resistant separator is all wound off from the wind-up roller and then wound up around the additional wind-up roller.

This procedure is, however, problematic in that it merely involves drawing a line on a heat-resistant separator original sheet with a marker in a case where an inspecting device has detected a defect in the heat-resistant separator original sheet. Thus, when an operator sees the line in the subsequent slitting step, the operator needs to stop the operation of winding off the heat-resistant separator original sheet and visually check the widthwise position of the defect. Enormous efforts are thus needed in order to specify the position of the defect in a plurality of heat-resistant separators prepared by cutting the heat-resistant separator original sheet.

Figure 5:
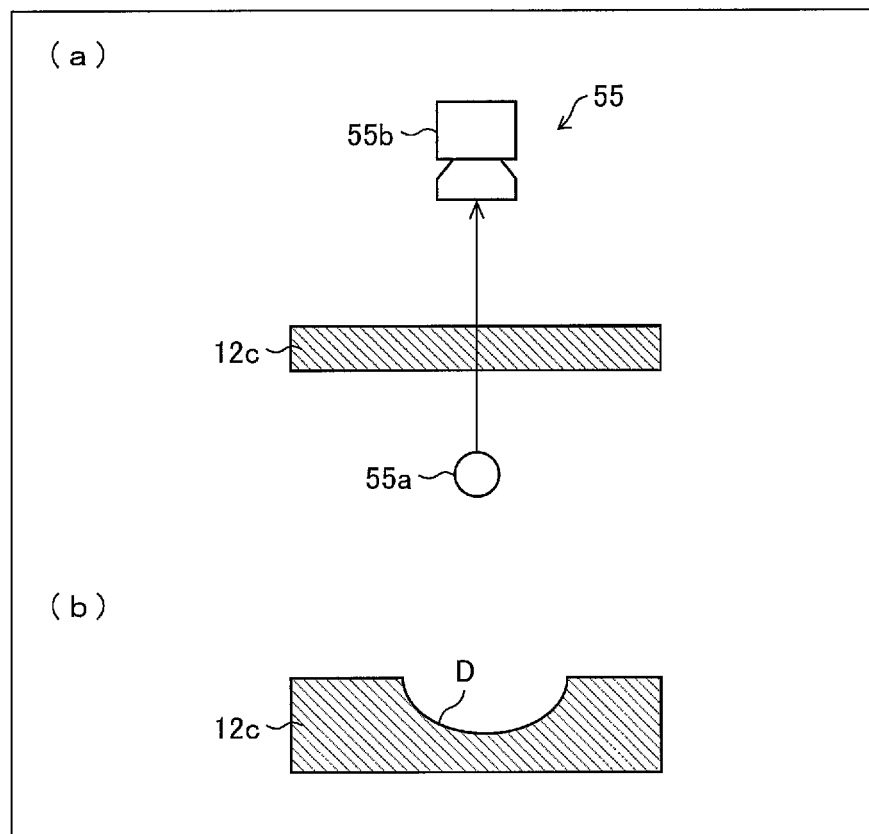
FIG. 5 provides diagrams illustrating a configuration of a base material defect inspecting device in the defect detecting step.
Figure 6:
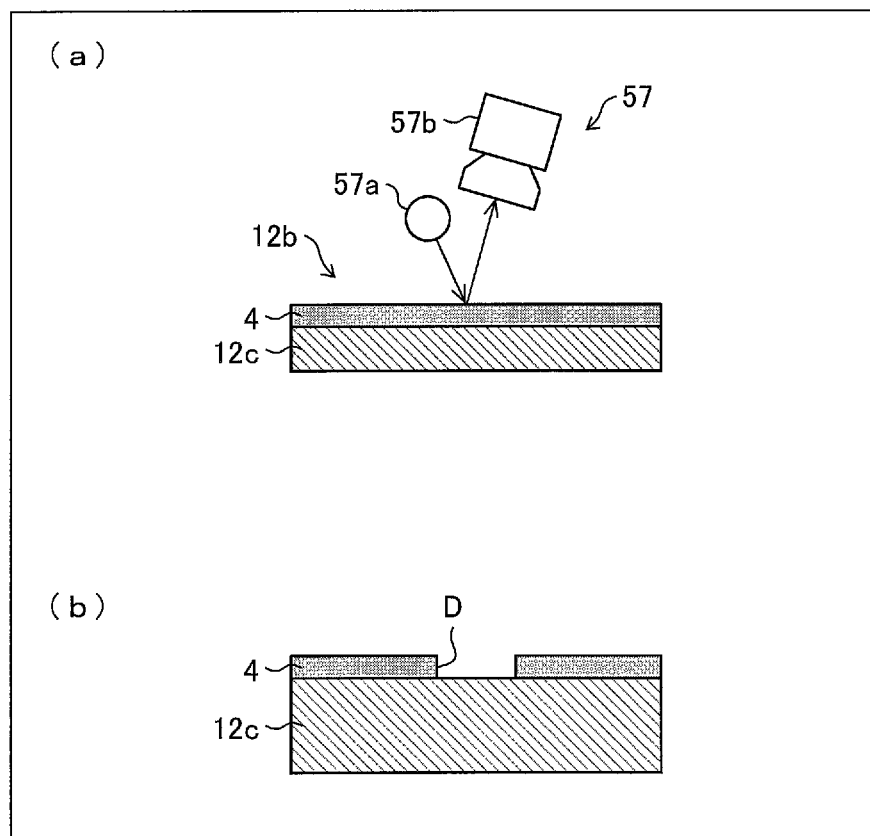
FIG. 6 provides diagrams illustrating a configuration of a coating defect inspecting device in the defect detecting step.
Figure 7:
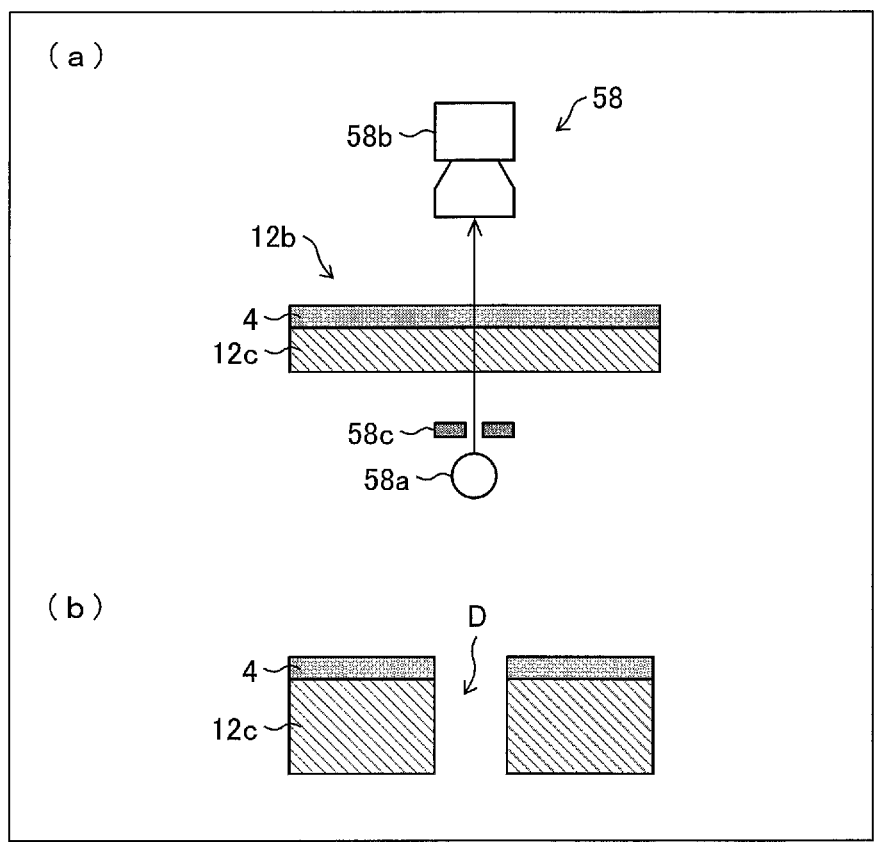
FIG. 7 provides diagrams illustrating a configuration of a pinhole defect inspecting device in the defect detecting step.

FIG. 4 provides diagrams schematically illustrating a defect detecting step and a defect information recording step both included in a method for marking a defect in the heat-resistant separator original sheet 12b. (a) of FIG. 4 is an elevational view of a conveying mechanism during the two steps, whereas (b) of FIG. 4 is a plan view of the conveying mechanism during the two steps. FIG. 5 provides diagrams illustrating a configuration of a base material defect inspecting device 55 in the defect detecting step. FIG. 6 provides diagrams illustrating a configuration of a coating defect inspecting device 57 in the defect detecting step. FIG. 7 provides diagrams illustrating a configuration of a pinhole defect inspecting device 58 in the defect detecting step.

A heat-resistant layer is formed on a separator original sheet 12c by the coating section 54 so that a heat-resistant separator original sheet 12b is prepared. The heat-resistant separator original sheet 12b is wound up around a core 53. Specifically, a base material inspecting step (defect detecting step) is a step of inspecting the separator original sheet 12c for a defect D. The base material inspecting step is carried out by a base material defect inspecting device 55 between a step of unreeling the separator original sheet 12c and the coating step. The base material defect inspecting device 55 includes a light source 55a and a detector 55b that are so positioned as to sandwich the separator original sheet 12c. The light source 55a emits light in a direction perpendicular to the front and back surfaces of the separator original sheet 12c, whereas the detector 55b detects light having passed through the separator original sheet 12c. This allows the base material defect inspecting device 55 to inspect the separator original sheet 12c for a defect D present therein (defect detecting step). The defect D present in the separator original sheet 12c is, for example, a through hole (pinhole), an inappropriate film thickness, or a defect caused by a foreign substance.

A coating inspecting step (defect detecting step) is a step of inspecting the heat-resistant layer 4, formed on the separator original sheet 12c, for a defect D. The coating inspecting step is carried out by a coating defect inspecting device 57 between the coating step and a step of winding up the heat-resistant separator original sheet 12b around the core 53. The coating defect inspecting device 57 includes a light source 57a and a detector 57b that are positioned on the side of the heat-resistant layer 4 of the heat-resistant separator original sheet 12b. The light source 57a emits light to the heat-resistant layer 4, whereas the detector 57b detects light having been reflected by the heat-resistant layer 4. This allows the coating defect inspecting device 57 to detect a defect D present in the heat-resistant layer 4. The defect D present in the heat-resistant layer 4 is, for example, a crease, peeling off, repellency, and a surface failure. The repellency refers to a defect of a foreign substance, oil, or the like on the surface of the separator original sheet 12c repelling the coating solution from the surface, with the result of local absence of a heat-resistant layer 4 or local formation of an extremely thin heat-resistant layer 4. The surface failure refers to a failure in the thickness of the heat-resistant layer 4.

A pinhole inspecting step (defect detecting step) is a step of inspecting the heat-resistant separator original sheet 12b for a defect D in the form of a pinhole. The pinhole inspecting step is carried out by a pinhole defect inspecting device 58 positioned between the coating defect inspecting device 57 and a defect information recording device 56. The pinhole defect inspecting device 58 includes a light source 58a, a detector 58b, and a slit 58c. The light source 58a is positioned on the side of the separator original sheet 12c of the heat-resistant separator original sheet 12b, and emits light in a direction perpendicular to the front and back surfaces of the heat-resistant separator original sheet 12b. The slit 58c lets the light pass therethrough and travel toward the heat-resistant separator original sheet 12b. The detector 58b detects a defect D on the basis of light having passed through the heat-resistant separator original sheet 12b. The defect D in the form of a pinhole has a diameter ranging from several hundreds of micrometers to several millimeters.

The production process involves a defect information recording device 56 positioned between the pinhole defect inspecting device 58 and the core 53. The defect information recording device 56 records, on the heat-resistant separator original sheet 12b, a defect code DC (second defect code) indicative of information on the position of any defect D detected by the base material defect inspecting device 55, the coating defect inspecting device 57, or the pinhole defect inspecting device 58. The defect information recording device 56 records such a defect code DC at a portion on a widthwise side of the heat-resistant separator original sheet 12b which portion corresponds to the lengthwise position of the defect D on the heat-resistant separator original sheet 12b. The defect code DC may be code data such as a two-dimensional code or QR Code (registered trademark). The information on the position indicates where the defect D is positioned in the lengthwise and width directions of the heat-resistant separator original sheet 12b. The information on the position may include information with which the type of the defect D is distinguishable. The type of a defect D is, for example, (i) a structural defect in the base material for which defect the base material defect inspecting device 55 inspects the separator original sheet 12c, (ii) a defect caused in the applying step for which defect the coating defect inspecting device 57 inspects the heat-resistant layer 4, or (iii) a defect in the form of an opening for which defect the pinhole defect inspecting device 58 inspects the heat-resistant separator original sheet 12b.

The defect information recording device 56 records a defect code DC at a portion on a widthwise side of a heat-resistant separator original sheet 12b which portion corresponds to the position of a defect D. The defect code DC has a lengthwise position that varies by ±ΔX depending on the speed at which the heat-resistant separator original sheet 12b is transferred. In a case where the transfer speed is, for example, 80 m/min, the lengthwise position of the defect code DC varies by approximately ±30 mm (ΔX=30 mm). A higher transfer speed leads to a wider range of variation of the position of the defect code DC (that is, larger ΔX), whereas a lower transfer speed leads to a narrower range of variation of the position of the defect code DC (that is, smaller ΔX). As described above, the lengthwise position of a defect code DC corresponding to the position of a defect D in the longitudinal direction of a heat-resistant separator original sheet 12b varies in a range depending on the speed at which the heat-resistant separator original sheet 12b is transferred.

The defect information recording device 56 (see FIG. 4) records a defect code DC indicative of information on the position of a defect D at a portion on a widthwise side of the heat-resistant separator original sheet 12b which portion corresponds to the lengthwise position of the defect D on the heat-resistant separator original sheet 12b. A defect D is separated from its corresponding defect code DC by a lengthwise distance $L_{MD}$ of, for example, preferably not more than 100 mm, more preferably not more than 30 mm. The defect code DC is separated from a widthwise side of the heat-resistant separator original sheet 12b by a distance LTD of, for example, preferably not more than 100 mm, more preferably not more than 30 mm. The distance LTD is preferably not less than 10 mm because the widthwise sides of the heat-resistant separator original sheet 12b easily become wavy.

The separator original sheet 12c or heat-resistant separator original sheet 12b is subjected to a film tension of typically not more than 200 N/m, preferably not more than 120 N/m. The term "film tension" refers to a tension applied to a film being conveyed, the tension being applied in the conveying direction over a unit widthwise length of the film. For instance, with a film tension of 200 N/m, a force of 200 N is applied to the film over a width of 1 m. A film tension of more than 200 N/m may form a wrinkle in the conveying direction of the film and decrease the accuracy of defect inspection. The film tension is typically not less than 10 N/m, preferably not less than 30 N/m. A film tension of less than 10 N/m may cause slack in the film or let the film meander. The separator original sheet 12c or heat-resistant separator original sheet 12b has pores P, and is subjected to a film tension lower than a film tension applied to a non-porous film such as an optical film. The separator original sheet 12c or heat-resistant separator original sheet 12b thus has a physical property of being stretchable more easily than a non-porous film such as an optical film. As such, in a case where a defect code DC is recorded at a portion on a widthwise side of the heat-resistant separator original sheet 12b which portion corresponds to the lengthwise position of the defect D on the heat-resistant separator original sheet 12b, the lengthwise position of the defect D is substantially not displaced from the lengthwise position of the defect code DC even in a case where the heat-resistant separator original sheet 12b has been stretched lengthwise. The lengthwise position of a defect D is thus easily specifiable even in the case where the heat-resistant separator original sheet 12b has been stretched lengthwise.

The heat-resistant separator original sheet 12b with a defect code DC recorded at a portion on a widthwise side thereof is wound up around the core 53. The core 53, around which the heat-resistant separator original sheet 12b has been wound up, is carried to a position for the subsequent slitting step.

(Slitting Apparatus)

The heat-resistant separator 12a, produced from the heat-resistant separator original sheet 12b (hereinafter referred to as "separator original sheet"), or the separator 12 (hereinafter referred to as "separator"), produced from the separator original sheet 12c, preferably has a width (hereinafter referred to as "product width") suitable for application products such as the lithium-ion secondary battery 1. For improved productivity, however, the separator original sheet is produced so as to have a width that is equal to or larger than a product width. Then, after having been once produced so as to have a width equal to or larger than the product width, the separator original sheet is cut (slit) into a separator(s) having the product width. Note that the expression "width of a/the separator" means a dimension of the separator in a direction that is parallel to a plane in which the separator extends and that is perpendicular to the longitudinal direction of the separator.

Figure 8:
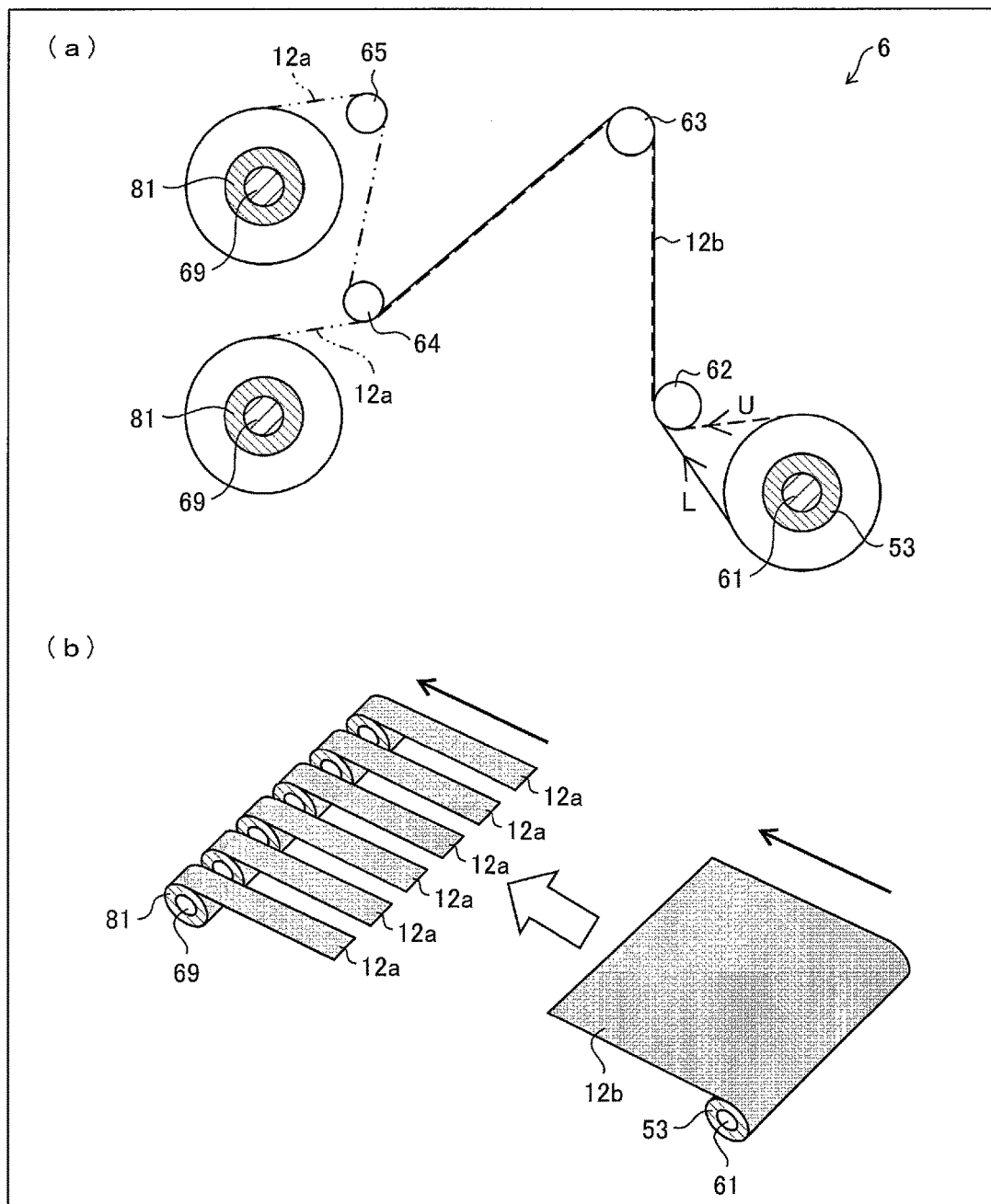
FIG. 8 provides diagrams schematically illustrating a configuration of a slitting apparatus configured to slit a separator.

FIG. 8 provides diagrams schematically illustrating a configuration of a slitting apparatus 6 configured to slit the separator original sheet 12b. (a) of FIG. 8 illustrates the entire configuration, and (b) of FIG. 8 illustrates an arrangement before and after slitting the separator original sheet 12b.

As illustrated in (a) of FIG. 8, the slitting apparatus 6 includes a rotatably supported cylindrical wind-off roller 61, rollers 62 to 65, and wind-up rollers 69. The slitting apparatus 6 is further provided with a cutting device 7 (see FIG. 9) described later.

(Before Slitting)

In the slitting apparatus 6, a cylindrical core 53 on which the separator original sheet 12b is wrapped is fit on the wind-off roller 61. As illustrated in (a) of FIG. 8, the separator original sheet 12b is wound off from the core 53 to a route U or L. The separator original sheet 12b thus wound off is conveyed to the roller 64 via the roller 63 at a speed of, for example, 100 m/min. In the conveying step, the separator original sheet 12b is slit lengthwise into a plurality of separators 12a.

(After Slitting)

As illustrated in (a) of FIG. 8, one or more of the plurality of separators 12a are wound up around respective cores 81 fit on the plurality of wind-up rollers 69. Further, another one or more of the plurality of separators 12a are wound up around respective cores 81 fit on the plurality of wind-up rollers 69. Note that each of the slit separators wound into a roll form is referred to as a "separator roll".

(Cutting Device)

Figure 9:
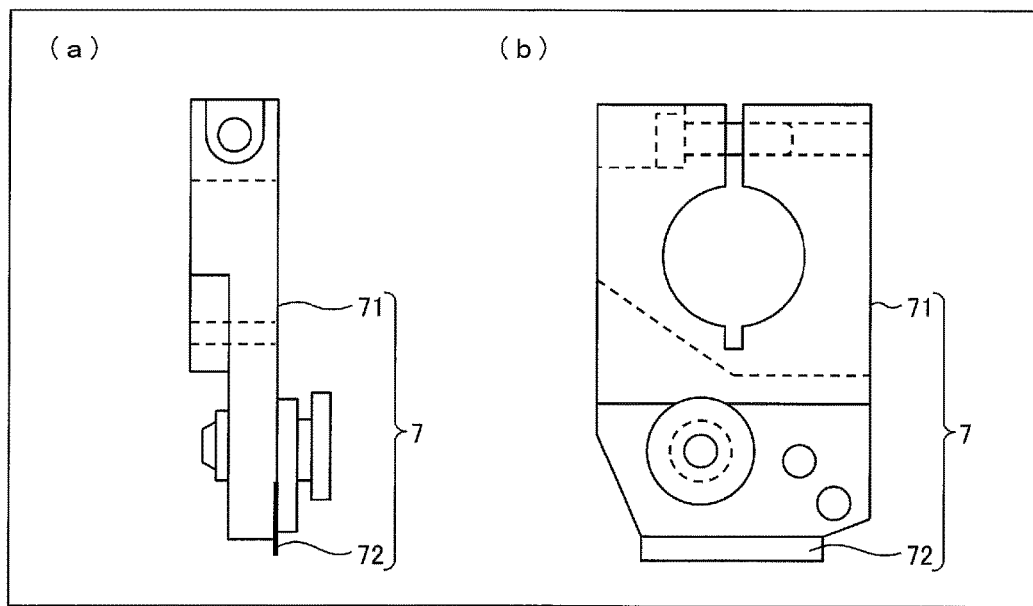
FIG. 9 provides a side view and an elevational view of a cutting device included in the slitting apparatus illustrated in FIG. 8.

FIG. 9 provides views each illustrating a configuration of the cutting device 7 of the slitting apparatus 6 illustrated in (a) of FIG. 8. (a) of FIG. 9 is a side view of the cutting device 7, and (b) of FIG. 9 is a front view of the cutting device 7.

As illustrated in (a) and (b) of FIG. 9, the cutting device 7 includes a holder 71 and a blade 72. The holder 71 is fixed to a housing or the like provided in the slitting apparatus 6. The holder 71 holds the blade 72 in such a manner that the blade 72 and the separator original sheet 12b being conveyed have a fixed positional relation. The blade 72 has a finely sharpened edge and slits the separator original sheet by using this edge.

Figure 10:
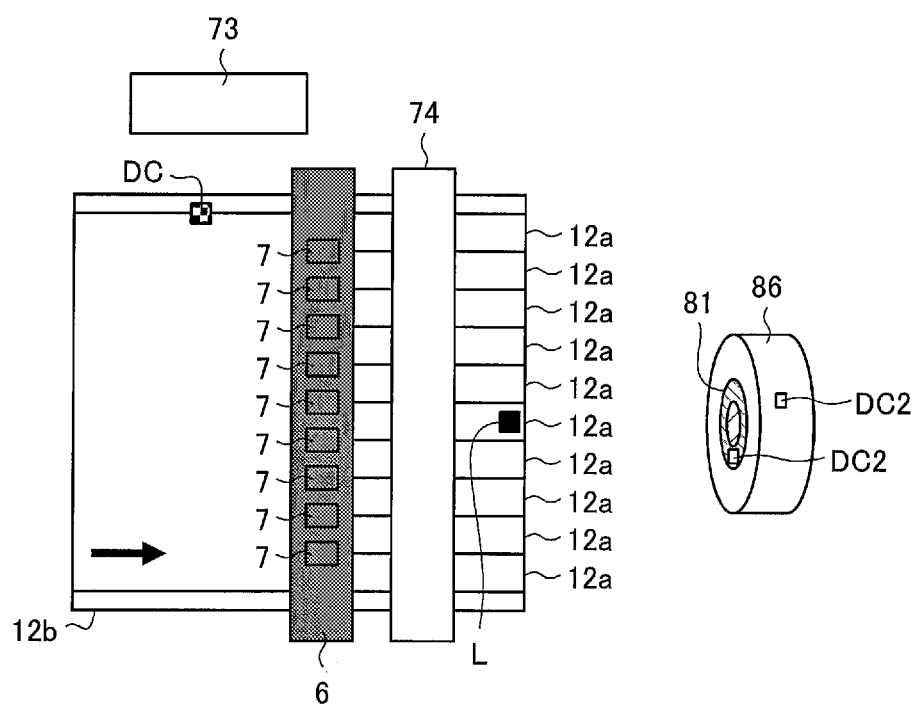
FIG. 10 is a diagram schematically illustrating a reading step, a mark providing step, and a wind-up step all included in a method for specifying the position of a defect in a separator.

FIG. 10 is a diagram schematically illustrating a reading step, a mark providing step, and a wind-up step all included in a method for specifying the position of a defect in a separator 12a. The separator original sheet 12b is wound off from the core 53 (see FIG. 8) at a fixed speed (for example, 80 m/min). A reading section 73 reads a defect code DC recorded at a portion on a widthwise side of the separator original sheet 12b (reading step). The plurality of cutting devices 7, included in the slitting apparatus 6, cut the separator original sheet 12b lengthwise to prepare a plurality of separators 12a (cutting step).

Next, a mark providing device 74 identifies one of the plurality of separators 12a, prepared by the plurality of cutting devices 7, on the basis of information on the widthwise position of a defect D which information is in the form of a defect code DC and has been read by the reading section 73. The mark providing device 74 then provides a mark L at a position corresponding to the defect D in the separator 12a identified as above (mark providing step). In a case where there are a plurality of defects D present, the mark providing device 74 identifies a plurality of separators 12a. The mark L is preferably a label, so the mark providing device 74 is preferably a labeler.

The mark L may be, instead of a label, a mark drawn with a pen or a mark applied by an injector. The mark L may also be a thermolabel, which is printed by heating the separator 12a (made of resin). The mark L may also be provided by forming a hole in the separator 12a with use of a laser.

The plurality of separators 12a, prepared by cutting the separator original sheet 12b with use of the cutting devices 7, are each wound up around one of a plurality of cores 81 (wind-up step).

The mark providing device 74 then records information on the position of the defect D in the lengthwise direction of the separator original sheet 12b, which defect D is indicated by a defect code DC. The mark providing device 74 records such information as a defect code DC2 (first defect code) on (i) an outermost portion 86 of the separator 12a identified and wound up and/or (ii) the core 81.

The defect code DC2 may be recorded on a side surface or outer layer of a separator 12a that has been wound up. The defect code DC2 may alternatively be recorded on a package of a roll including a core 81 and a separator 12a that has been wound up. In a case where the core 81 has a double structure including an inner cylinder and an outer cylinder and having a space therebetween, the defect code DC2 may be recorded on a portion that faces the space. In a case where the defect code DC2 is to be recorded on an outer layer of the separator 12a, the defect code DC2 is preferably recorded on the outermost portion 86 on the front side of the outermost layer as illustrated in FIG. 10. The defect code DC2 may, however, be recorded on at least a portion that can be easily exposed to the outside of the roll (for example, one or two layers inside the outermost layer). The defect code DC2 is not necessarily recorded on the front side of the separator 12a, and may be recorded on the back side thereof. The defect code DC2 is, however, preferably so recorded as to be visible from the outside of the roll.

Further alternatively, the defect code DC2 may be recorded on a member such as a tag to be attached to the core 81 or the like.

The defect code DC2 includes information on the position of the defect D in a separator 12a which information is based on the information on the position of the defect D (see FIG. 4) in the separator original sheet 12b which position is indicated by the defect code DC. The defect code DC indicates information on the position of a defect D in the lengthwise and width directions of the separator original sheet 12b. There may be a plurality of defect codes DC along the full length of the separator original sheet 12b in correspondence with detection of defects D. The defect code DC2 can thus include information on the respective positions of a plurality of defects D in the entire separator 12a. The defect code DC2 thus includes information on the respective positions of a plurality of defects D in the entire roll including a core 81 and a separator 12a wound around the core 81. The defect code DC2 preferably includes information on the respective positions of all defects D in the entire roll. Such a defect code DC2, which includes information on the respective positions of a plurality of defects D in the entire roll, may be recorded at any portion of the separator 12a or core 81.

A separator 12a wound around a core 81 includes an inner layer and an outer layer. The defect code DC2 simply needs to include information on the respective positions of a plurality of defects D present in at least one of the inner layer and the outer layer, which are included in a separator 12a wound around a core 81.

As described above, reading a defect code DC2 recorded on a roll makes it possible to easily specify the respective positions of a plurality of defects D in at least one of the inner layer and the outer layer of the separator 12a. Further, reading a defect code DC2 that is recorded on a portion that can be easily exposed to the outside of the roll and that includes information on the respective positions of a plurality of defects D in the roll makes it possible to easily specify the respective positions of a plurality of defects D inside the roll.

Figure 11:
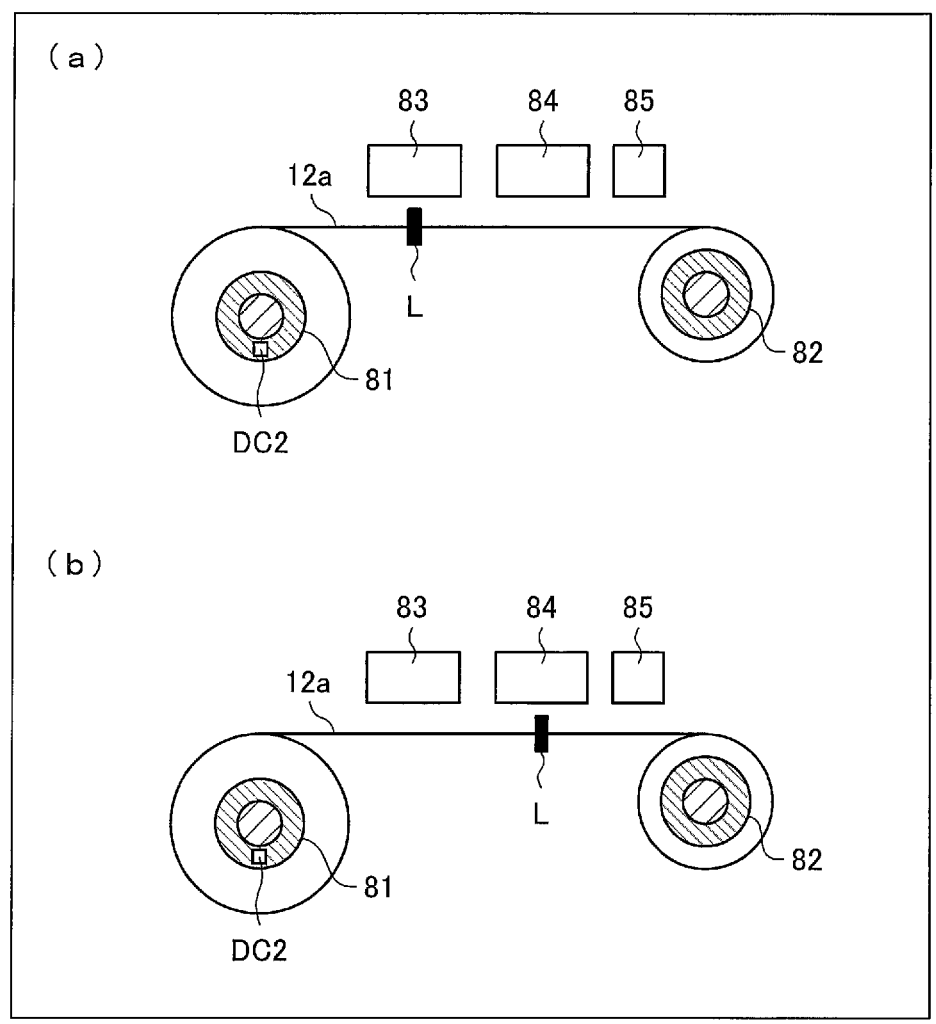
FIG. 11 provides diagrams schematically illustrating a mark sensing step and a defect removing step both included in a method for specifying the position of a defect in a separator.

FIG. 11 provides diagrams schematically illustrating a mark sensing step and a defect removing step both included in a method for specifying the position of a defect in a separator 12a. (a) of FIG. 11 is a diagram schematically illustrating the mark sensing step. (b) of FIG. 11 is a diagram schematically illustrating the defect removing step. First, a mark sensing device 83 reads a defect code DC2 recorded on the outermost portion 86 and/or core 81. The mark providing device 74 receives information read by the mark sensing device 83 and attaches a mark L to the separator 12a with the defect D present therein. The mark sensing step then starts an operation of winding off the separator 12a from the core 81 and winding up the heat-resistant separator 12a again around a core 82. Next, the mark sensing device 83, on the basis of information on the position of the defect D (indicated by the defect code DC2 read by the mark sensing device 83) in the lengthwise direction of the separator original sheet 12b, slows the above operation when the defect D has become close to the core 82.

The mark sensing device 83 then senses the mark L, which is attached to the position corresponding to the defect D in the separator 12a (mark sensing step). When the mark sensing device 83 has sensed the mark L, the mark sensing device 83 stops the operation of winding up the separator 12a again. Then, a defect removing device 84 cuts the separator 12a widthwise at (i) a position upstream of the defect D (which corresponds to the mark L) and (ii) a position downstream of the defect D, and removes the defect D from the separator 12a (defect removing step). The defect removing step may alternatively be carried out manually by an operator instead of the defect removing device 84. Then, a connecting device 85 connects two portions of the separator 12a that are separated from each other as the result of cutting the separator 12a (connecting step). The connecting step may alternatively be carried out manually by an operator instead of the connecting device 85. Next, the connecting device 85 resumes the operation of winding up the separator 12a again. The operation of winding off the separator 12a from the core 81 and winding up the separator 12a again around the core 82 is then completed. The two portions of the separator 12a, which result from dividing the separator 12a, may alternatively be left unconnected to be individually wound up around separate cores. In other words, the separator 12a may be wound up again in such a manner that that portion of the separator 12a which is downstream of the removed portion is wound up around the core 82, whereas that portion of the separator 12a which is upstream of the removed portion is wound up around another core.

Embodiment 2

Embodiment 1 is an example in which information on the position of a defect D present in a separator original sheet 12b is recorded at a widthwise end of the separator original sheet 12b. The present invention is, however, not limited to such a configuration, and may be configured such that information on the position of a defect D is recorded in an information storing device.

Figure 12:
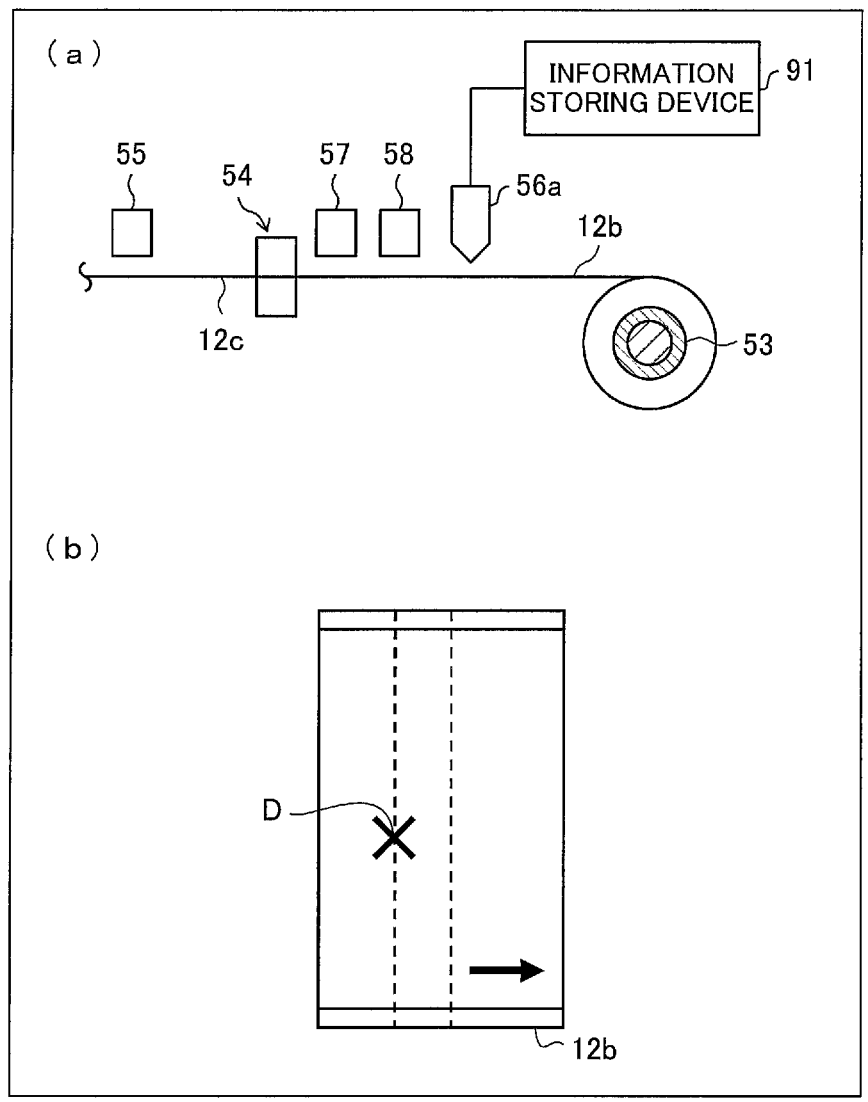
FIG. 12 provides diagrams schematically illustrating a defect detecting step and a defect information recording step both included in a method in accordance with Embodiment 2 for marking a defect in a separator original sheet.
Figure 13:
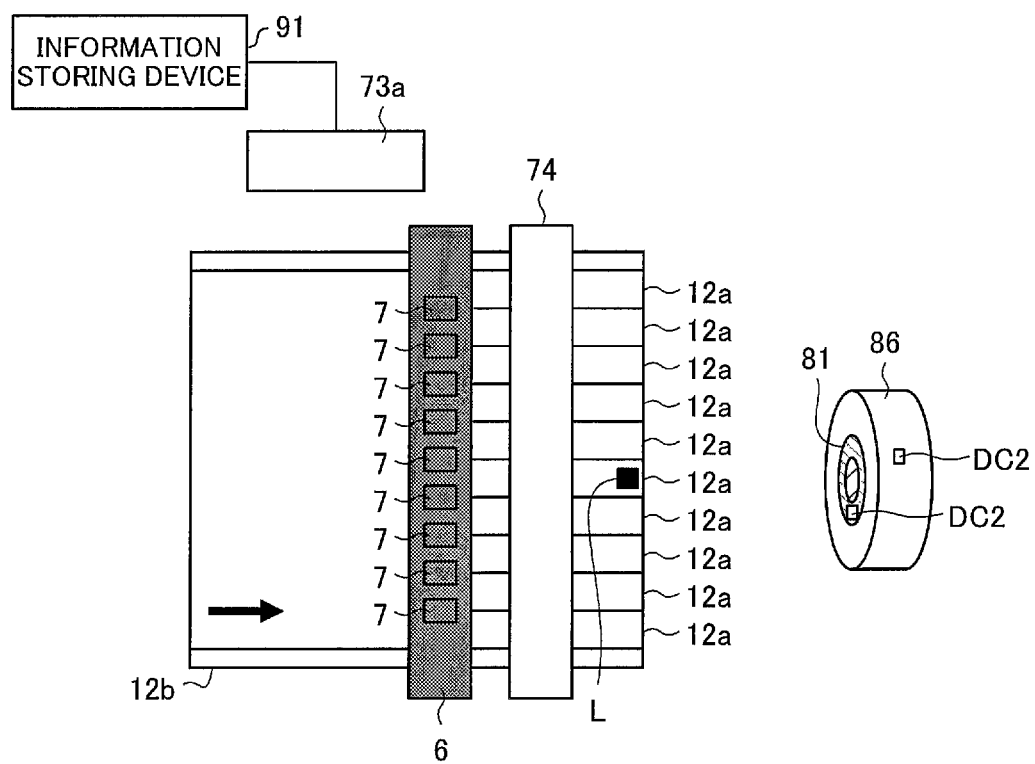
FIG. 13 is a diagram schematically illustrating a reading step, a mark providing step, and a wind-up step all included in a method for specifying the position of a defect in a separator.

FIG. 12 provides diagrams schematically illustrating a defect detecting step and a defect information recording step both included in a method in accordance with Embodiment 2 for marking a defect in a separator original sheet 12b. FIG. 13 is a diagram schematically illustrating a reading step, a mark attaching step, and a wind-up step all included in a method for specifying the position of a defect in a separator 12a. Any constituent element of Embodiment 2 that is identical to a corresponding constituent element described earlier for Embodiment 1 is assigned a common reference sign, and is not described in detail here.

A defect information recording device 56a (defect information recording section, separator original sheet producing apparatus) records, in an information storing device 91, positional information indicative of the lengthwise and widthwise positions of a defect D that is present in the separator original sheet 12c or 12b and that has been detected by the base material defect inspecting device 55, the coating defect inspecting device 57, or the pinhole defect inspecting device 58. A reading section 73a reads the positional information from the information storing device 91 (reading step).

Embodiment 3

Figure 14:
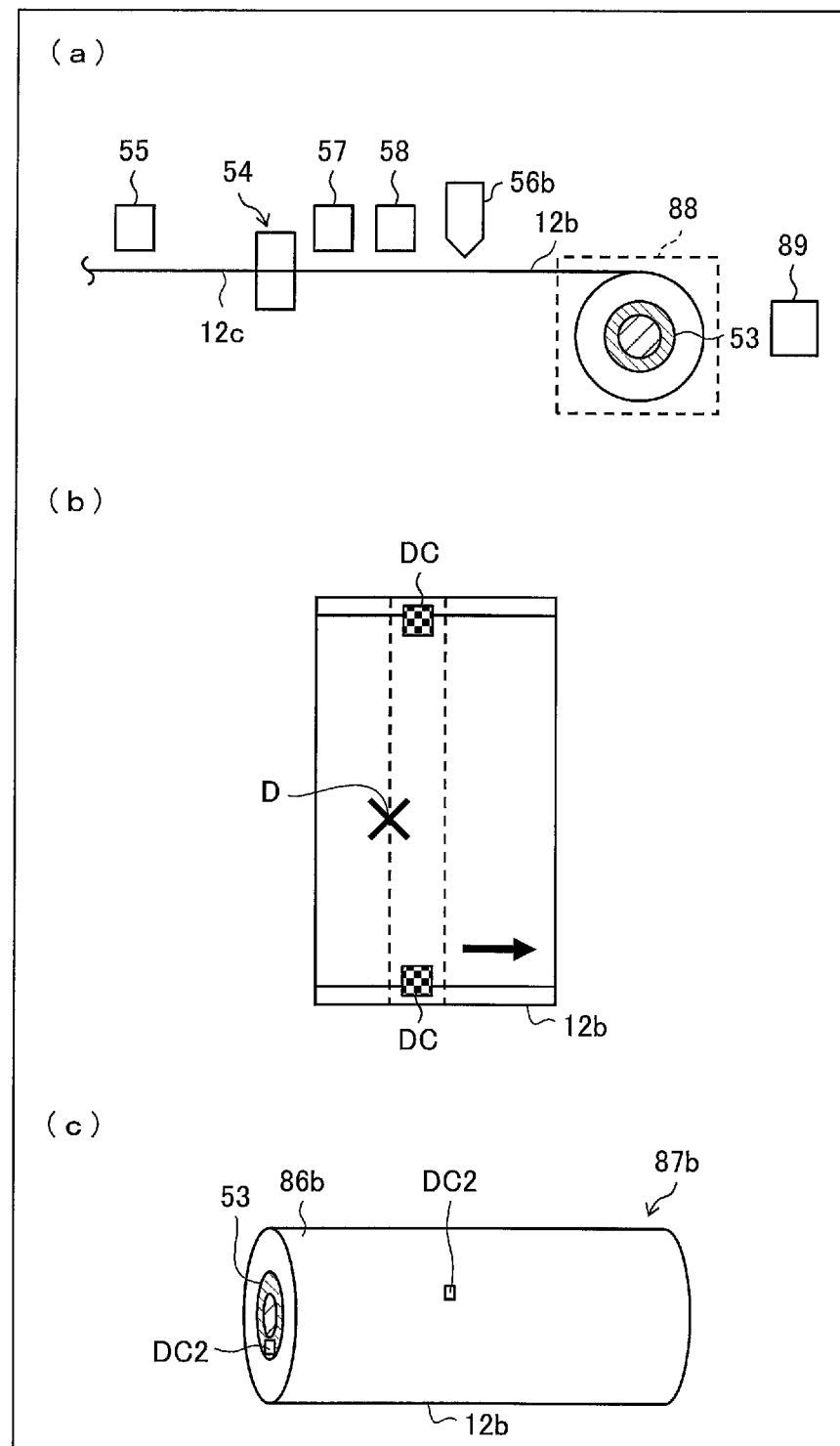
FIG. 14 provides diagrams schematically illustrating a defect detecting step and a defect information recording step both included in a method in accordance with Embodiment 3 for marking a defect in a separator original sheet.

FIG. 14 provides diagrams schematically illustrating a defect detecting step and a defect information recording step both included in a method in accordance with Embodiment 3 for marking a defect in a separator original sheet 12b. (a) of FIG. 14 is an elevational view of a conveying mechanism during the two steps. (b) of FIG. 14 is a plan view of the conveying mechanism during the two steps. (c) of FIG. 14 is a perspective view of a separator original sheet roll 87b (separator roll) including a separator original sheet 12b wound up after the two steps. Any constituent element of Embodiment 3 that is identical to a corresponding constituent element described earlier for Embodiment 1 is assigned a common reference sign, and is not described in detail here.

Embodiment 1 describes with reference to FIG. 4 an example in which a defect code DC indicative of information on the position of a defect D is recorded at a widthwise end of a separator original sheet 12b. The present invention is, however, not limited to such a configuration, and may alternatively be configured as illustrated in (a) and (b) of FIG. 14 such that (i) a pair of defect information recording devices 56b are provided at respective positions corresponding to the opposite widthwise ends of a separator original sheet 12b and that (ii) a defect code DC is recorded at each of the opposite widthwise ends of the separator original sheet 12b. Such two defect codes DC may be recorded at respective portions on the opposite widthwise sides of the separator original sheet 12b which portions correspond to the position of the defect D in the longitudinal direction of the separator original sheet 12b. This allows the position of a defect code DC to indicate the position of a defect D in the longitudinal direction of a separator original sheet 12b.

In a case where defect codes DC have been recorded at respective opposite widthwise ends of a separator original sheet 12*b*, it is only necessary to normally read at least one of the two defect codes DC. This allows the reading section 73 illustrated in FIG. 10 to read a defect code DC more reliably. In a case where, for example, one of the widthwise ends of a separator original sheet 12*b* has been wrinkled or one of the defect codes DC has disappeared, the reading section 73 can read the other defect code DC.

Embodiment 1 describes with reference to FIG. 10 an example in which a defect code DC2 is recorded on (i) the outermost portion 86 of a separator 12*a* wound around a core 81 and having a defect D and/or (ii) the core 81, around which the separator 12*a* is wound. The present invention is, however, not limited to such a configuration, and may alternatively be configured as illustrated in (c) of FIG. 14 to produce a separator original sheet roll 87*b* (separator roll) having a defect code DC2 that is recorded on (i) the outermost portion 86*b* of a separator original sheet 12*b* wound around a core 53 and having a defect D and/or (ii) the core 53, around which the separator original sheet 12*b* is wound, and that indicates information on the position of a defect D in the lengthwise direction of the separator original sheet 12*b*.

A separator original sheet 12*b* having a defect D detected is wound up around a core 53 by a wind-up section 88. Then, a defect code recording section 89 (first defect code providing section) records, on the outermost portion 86*b* of the separator original sheet 12*b* (which has been wound around the core 53) or the core 53 (around which the separator original sheet 12*b* has been wound), a defect code DC2 including information on the position of the defect D in the longitudinal direction of the separator original sheet 12*b*.

The defect code DC2 may be recorded on a side surface or outer layer of a separator original sheet 12*b* that has been wound up. The defect code DC2 may alternatively be recorded on a package of a separator original sheet roll 87*b* including a core 53 and a separator original sheet 12*b* that has been wound up. In a case where the core 53 has a double structure including an inner cylinder and an outer cylinder and having a space therebetween, the defect code DC2 may be recorded on a portion that faces the space. In a case where the defect code DC2 is to be recorded on an outer layer of the separator original sheet 12*b*, the defect code DC2 is preferably recorded on the outermost portion 86*b* on the front side of the outermost layer as illustrated in (b) of FIG. 14. The defect code DC2 may, however, be recorded on at least a portion that can be easily exposed to the outside of the separator original sheet roll 87*b* (for example, one or two layers inside the outermost layer). The defect code DC2 is not necessarily recorded on the front side of the separator original sheet 12*b*, and may be recorded on the back side thereof. The defect code DC2 is, however, preferably so recorded as to be visible from the outside of the separator original sheet roll 87*b*.

Further alternatively, the defect code DC2 may be recorded on a member such as a tag to be attached to the core 53 or the like.

The defect information recording devices 56*b* may each be configured to record a defect code DC2 at such a position on a separator original sheet 12*b* being conveyed before being wound up that the defect code DC2 is on the outermost portion 86*b* of the separator original sheet 12*b* having been wound up. In this case, the separator original sheet 12*b* may be cut widthwise after being wound up around the core 53 so that the defect code DC2 is on the outermost portion 86*b* of the separator original sheet 12*b* having been wound up.

The defect code DC2 includes information on the position of a defect in a separator original sheet 12*b* which defect is indicated by a defect code DC. The defect code DC indicates information on the position of a defect D in the lengthwise and width directions of the separator original sheet 12*b*. There may be a plurality of defect codes DC along the full length of the separator original sheet 12*b* in correspondence with detection of defects D. The defect code DC2 can thus include information on the respective positions of a plurality of defects D in the entire separator original sheet 12*b*. The defect code DC2 thus includes information on the respective positions of a plurality of defects D in the entire separator original sheet roll 87*b* including a core 53 and a separator original sheet 12*b* wound around the core 53. The defect code DC2 preferably includes information on the respective positions of all defects D in the entire separator original sheet roll 87*b*. Such a defect code DC2, which includes information on the respective positions of a plurality of defects D in the entire separator original sheet roll 87*b*, may be recorded at any portion of the separator original sheet 12*b* or core 53.

A separator original sheet 12*b* wound around a core 53 includes an inner layer and an outer layer. The defect code DC2 simply needs to include information on the respective positions of a plurality of defects D present in at least one of the inner layer and the outer layer, which are included in a separator original sheet 12*b* wound around a core 53.

As described above, reading a defect code DC2 recorded on a separator original sheet roll 87*b* makes it possible to easily specify the respective positions of a plurality of defects D in at least one of the inner layer and the outer layer of the separator original sheet 12*b*. Further, reading a defect code DC2 that is recorded on a portion that can be easily exposed to the outside of the separator original sheet roll 87*b* and that includes information on the respective positions of a plurality of defects D in the separator original sheet 12*b* makes it possible to easily specify the respective positions of a plurality of defects D inside the separator original sheet roll 87*b*.

Figure 15:
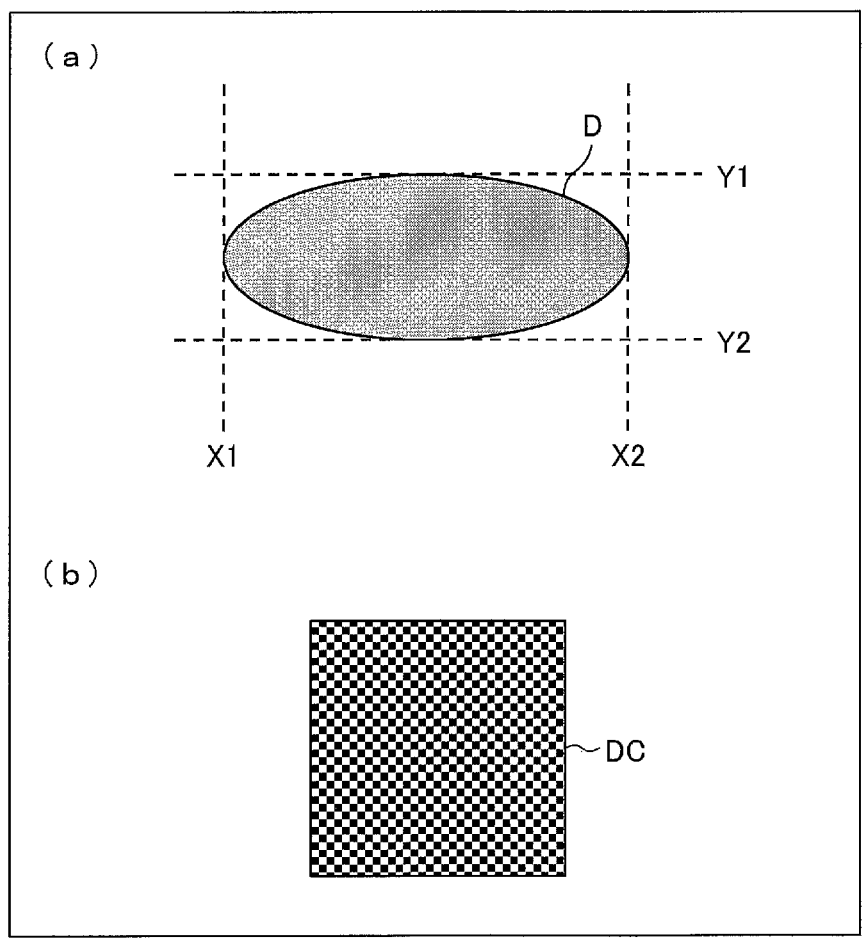
FIG. 15 provides diagrams illustrating a form of a defect code in accordance with Embodiment 3.

FIG. 15 provides diagrams illustrating a form of a defect code DC in accordance with Embodiment 3. The defect code DC is similar in arrangement for Embodiments 1 and 2 as well. The defect code DC2 may also be similar in arrangement as well. The defect code DC (see (b) of FIG. 15) includes information on a minimum coordinate value X1, a maximum coordinate value X2, a minimum coordinate value Y2, and a maximum coordinate value Y1 all corresponding to a defect D (see (a) of FIG. 15). The defect code DC includes information on the number and type(s) of defects D. As described earlier, the types of defects D include a through hole (pinhole), an inappropriate film thickness, and a defect caused by a foreign substance. In a case where the number of defects D is two or more, the defect code DC includes information on a minimum coordinate value X1, a maximum coordinate value X2, a minimum coordinate value Y2, and a maximum coordinate value Y1 for each defect D.

If one defect code DC is recorded for each defect D, such defect codes DC will unfortunately overlap with each other in a case where there are consecutive defects D present at short intervals in the longitudinal direction of a separator. In view of that, Embodiment 3 sets a minimum interval for recording defect codes DC on a separator at which interval or shorter no consecutive defect codes DC are recorded.

The defect code DC is in the form of a two-dimensional bar code. Examples of the two-dimensional bar code include a QR Code (registered trademark) and a data matrix.

Embodiment 4

Figure 16:
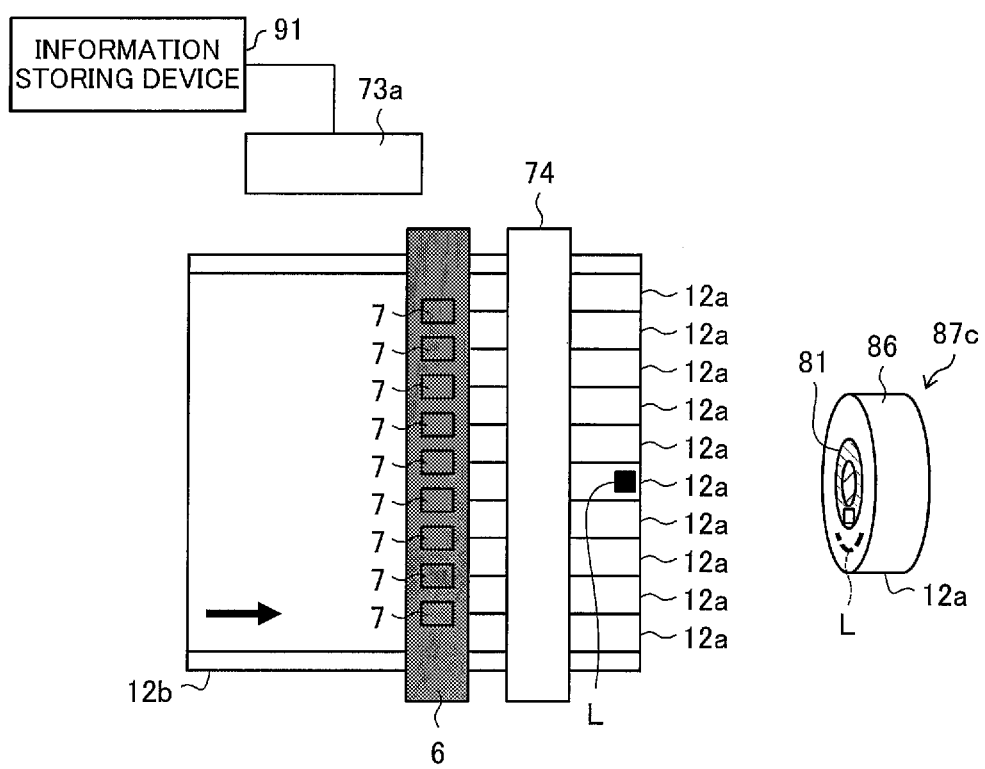
FIG. 16 is a diagram schematically illustrating a reading step, a mark providing step, and a wind-up step all included in a method in accordance with Embodiment 4 for specifying the position of a defect in a separator.

FIG. 16 is a diagram schematically illustrating a reading step, a mark providing step, and a wind-up step all included in a method in accordance with Embodiment 4 for specifying the position of a defect in a separator.

FIG. 10 and (c) of FIG. 14 above each illustrate an example in which a defect code DC2 is recorded on the outermost portion 86 of a separator 12a and/or a core 81. The present invention is, however, not limited to such a configuration, and may alternatively be configured as illustrated in FIG. 16 to produce a separator roll 87c that includes a core 81 and a separator 12a wound around the core 81 and having a mark L simply provided thereon instead of a defect code DC2 on the outermost portion 86 and/or core 81.

A separator roll 87c, from which no defective portion has been removed and on which a mark L has been provided as described above, is shipped to a user, who then cuts off any defective portion for integration with electrodes for a lithium-ion secondary battery. At this stage, a separator roll 87c having a defect therein may be used as follows: The separator 12a is not wound off and wound up again. After a defective portion has been cut off, cut parts of the separator 12a are not connected to each other, either. Instead, the separator 12a is wound off until a defect appears. This defective portion is cut off. Then, a portion with no defect therein is pulled out to resume the integration with electrodes. As described above, a separator roll 87c, from which no defective portion has been cut off, does not require the step of winding off a separator and winding up the separator again, as compared with a separator roll from which any defective portion has been cut off. This arrangement produces the effect of reducing the process load on a separator, which is soft and easily suffers from a defect such as a wrinkle.

(Other Aspects of the Present Invention)

In order to attain the above object, a separator original sheet producing method in accordance with the present invention includes the steps of: forming a separator original sheet; detecting a defect in the separator original sheet; recording defect information including information on a first position of the defect which first position is a position in a width direction of the separator original sheet. The term "separator original sheet" refers to a wide separator that has not been slit.

The above feature involves recording defect information including information on a first position of a defect which first position is a position in the width direction of a separator original sheet. Referring to information recorded as such makes it possible to easily specify the position of a defect in a separator original sheet. This in turn makes it possible to easily remove a defect in a separator original sheet.

The separator original sheet producing method in accordance with the present invention may preferably be arranged such that the defect information further includes information on a second position of the defect which second position is a position in a longitudinal direction of the separator original sheet. The expression "longitudinal direction of the separator original sheet" refers to the direction in which a workpiece is conveyed during a process of producing a separator.

The above arrangement makes it possible to, on the basis of the information on the second position, easily find the defect when the separator original sheet is wound off.

The separator original sheet producing method in accordance with the present invention may preferably be arranged such that the defect information is recorded at a portion of the separator original sheet which portion corresponds to a second position of the defect which second position is a position in a longitudinal direction of the separator original sheet.

The above arrangement makes it possible to specify the second position of a defect on the basis of the position at which defect information has been recorded. Further, the defect information is recorded at a portion of the separator original sheet which portion corresponds to the second position of the defect. Thus, even in a case where the separator original sheet has been stretched lengthwise, the lengthwise position of the defect is substantially not displaced from the lengthwise position of the defect information. The lengthwise position of a defect is thus easily specifiable even in the case where the separator original sheet has been stretched lengthwise.

In order to attain the above object, a separator producing method in accordance with the present invention includes the steps of: (a) forming a separator original sheet; (b) detecting a defect in the separator original sheet; (c) recording defect information including information on a first position of the defect which first position is a position in a width direction of the separator original sheet; (d) cutting the separator original sheet having the defect, of which the information has been recorded in the step (c), in a longitudinal direction of the separator original sheet into a plurality of separators; (e) reading the information; and (f) on a basis of the information read in the step (e), providing at least one of the plurality of separators with a mark for specifying a position of the defect.

This feature involves providing, on the basis of the information read in the step (e), at least one of the plurality of separators with a mark for specifying the position of a defect. This makes it possible to easily remove a defective portion of a separator among the plurality of separators, prepared by slitting a separator original sheet, which separator has the defect.

The separator producing method in accordance with the present invention may preferably further include the steps of: (g) winding up the at least one of the plurality of separators, which at least one of the plurality of separators has been provided with the mark; (h) sensing the mark while carrying out an operation of winding off the at least one of the plurality of separators, which has been wound up in the step (g), and winding up the at least one of the plurality of separators again; and (g) in accordance with the sensing of the mark, stopping the operation and removing the defect.

The above arrangement, which involves removing a defect after the separator is wound up, eliminates the need to stop the winding and thus improves the working efficiency.

The separator producing method in accordance with the present invention may preferably be arranged such that in the step (i): the at least one of the plurality of separators is cut in the width direction at two positions opposite to each other in the longitudinal direction with the defect therebetween; the defect is removed; and cut parts of the separator are then connected.

The above arrangement makes it possible to remove a defect in a separator original sheet for separator production.

The separator producing method in accordance with the present invention may preferably be arranged such that in the step (c), the information is recorded at a widthwise end of the separator original sheet.

The above arrangement makes it possible to recognize a defective portion by simply reading information recorded at a widthwise end of a separator original sheet.

The separator producing method in accordance with the present invention may preferably be arranged such that in the step (c), the information is recorded in an information storing device.

The above arrangement makes it possible to recognize a defective portion by reading information recorded in an information storing device.

The separator producing method in accordance with the present invention may preferably be arranged such that the step (f) is carried out by attaching a label.

In order to attain the above object, a separator original sheet in accordance with the present invention includes: at a widthwise end thereof, information on a position of a defect in the separator original sheet which position is a position in a width direction.

In order to attain the above object, a separator original sheet producing apparatus in accordance with the present invention includes: a forming section configured to form a separator original sheet; a defect detecting section configured to detect a defect in the separator original sheet; and a defect information recording section configured to record defect information including information on a position of the defect which position is a position in a width direction of the separator original sheet.

(Still Other Aspects of the Present Invention)

In order to attain the above object, a separator producing method in accordance with the present invention includes the steps of: winding up a separator, having a plurality of defects detected, around a core to form a roll including the core and the separator wound around the core; and providing the roll with a first defect code including information on respective positions of the plurality of defects in at least one of an inner layer and an outer layer of the separator wound around the core.

With this feature, reading a first defect code on a roll makes it possible to easily specify the respective positions of a plurality of defects in at least one of the inner layer and the outer layer of a separator.

The separator producing method in accordance with the present invention may preferably be arranged such that the first defect code includes information on respective positions of all defects detected in the separator.

With the above arrangement, reading a first defect code on a roll makes it possible to easily specify the respective positions of all defects in a separator wound around a core.

The separator producing method in accordance with the present invention may preferably be arranged such that the first defect code is provided on (i) the core, (ii) a side surface of the separator wound around the core, (iii) an outer layer of the separator wound around the core, or (iv) a package of a roll including the core and the separator wound around the core.

With the above arrangement, reading a first defect code that is provided on a portion that can be easily exposed to the outside of a roll and that includes information on the respective positions of a plurality of defects in the separator makes it possible to easily specify the respective positions of the plurality of defects inside the roll.

The present invention is not limited to the embodiments, but can be altered by a skilled person in the art within the scope of the claims. Any embodiment derived from a proper combination of technical means disclosed in different embodiments is also encompassed in the technical scope of the present invention.

INDUSTRIAL APPLICABILITY

The present invention is applicable to (i) a method for marking a defect in a separator original sheet for use in a lithium-ion secondary battery, (ii) a method for specifying the position of a defect in a separator, (iii) a separator roll, and (iv) a separator original sheet producing apparatus.

REFERENCE SIGNS LIST

4 Heat-resistant layer
6 Slitting apparatus
7 Cutting device
12 Separator
12a Heat-resistant separator (separator)
12b Heat-resistant separator original sheet (separator original sheet, separator)
12c Separator original sheet
53 Core
54 Coating section
55 Base material defect inspecting device
57 Coating defect inspecting device
58 Pinhole defect inspecting device
56, 56a, 56b Defect information recording device
73 Reading section
74 Mark providing device
81 Core
82 Core
83 Mark sensing device
84 Defect removing device
85 Connecting device
86, 86b Outermost portion
87 Separator roll
87b Separator original sheet roll (separator roll)
87c Separator roll
88 Wind-up section (separator original sheet producing apparatus)
89 Defect code recording section (first defect code providing section, separator original sheet producing apparatus)
91 Information storing device
D Defect
DC Defect code (second defect code)
DC2 Defect code (first defect code)
L Mark

The invention claimed is:

1. A separator original sheet producing method, comprising the steps of:
    winding up, around a core, a separator original sheet having a defect detected;
    providing a first defect code, including information on a first position of the defect which first position is a physical position in a longitudinal direction of the separator original sheet, on (i) the core, (ii) a side surface of the separator original sheet wound around the core, (iii) an outer layer of the separator original sheet wound around the core, or (iv) a package of a roll including the core and the separator original sheet wound around the core; and
    providing a second defect code, including information on a second position of the defect which second position is a physical position in a width direction of the separator original sheet, at each of opposite widthwise ends of the separator original sheet.

2. The separator original sheet producing method according to claim 1, wherein
    the second defect code is provided at a position indicative of the first position.

3. A separator producing method, comprising the steps of:
    (a) cutting a separator original sheet, having a defect detected, in a longitudinal direction of the separator original sheet into a plurality of separators;

(b) winding up, around a core, a separator among the plurality of separators which separator has the defect;

(c) providing a first defect code, including information on a first position of the defect which first position is a physical position in a longitudinal direction of the separator, on (i) the core, (ii) a side surface of the separator wound around the core, (iii) an outer layer of the separator wound around the core, or (iv) a package of a roll including the core and the separator wound around the core; and (d) providing a second defect code, including information on a second position of the defect which second position is a physical position in a width direction of the separator, at each of opposite widthwise ends of the separator.

4. The separator producing method according to claim 3, wherein
the second defect code is provided at a position indicative of a position of the defect which position is a position in the longitudinal direction of the separator original sheet.

5. The separator producing method according to claim 3, further comprising the steps of:

(e) providing the separator with a mark for specifying a position of the defect;

(f) sensing the mark while carrying out an operation of winding off the separator, which is present after the step (c), and winding up the separator again; and (g) in accordance with the sensing of the mark, stopping the operation and removing the defect.

6. The separator producing method according to claim 5, wherein
in the step (f), the first defect code is read, and when the defect has become close to the outer layer, the operation is slowed in correspondence with the first position.

7. The separator producing method according to claim 5, wherein
the step (e) is carried out by attaching a label.

8. A separator original sheet roll, comprising:
a core;
a separator original sheet having a defect and wound around the core;
a first defect code that is provided physically on (i) the core, (ii) a side surface of the separator original sheet wound around the core, (iii) an outer layer of the separator original sheet wound around the core, or (iv) a package of a roll including the core and the separator original sheet wound around the core and that includes information on a first position of the defect which first position is a position in a longitudinal direction of the separator original sheet; and
a second defect code that is provided physically at each of opposite widthwise ends of the separator original sheet and that includes information on a second position of the defect which second position is a position in a width direction of the separator original sheet.

9. A separator original sheet producing apparatus, comprising:
a wind-up section configured to wind up, around a core, a separator original sheet having a defect detected;
a first defect code providing section configured to provide a first defect code, including information on a first position of the defect which first position is a physical position in a longitudinal direction of the separator original sheet, on (i) the core, (ii) a side surface of the separator original sheet wound around the core, (iii) an outer layer of the separator original sheet wound around the core, or (iv) a package of a roll including the core and the separator original sheet; and
a second defect code providing section configured to provide a second defect code, including information on a second position of the defect which second position is a physical position in a width direction of the separator original sheet, at each of opposite widthwise ends of the separator original sheet.

* * * * *